United States Patent
Tanabe et al.

(10) Patent No.: US 9,650,615 B2
(45) Date of Patent: May 16, 2017

(54) PRACTICAL METHOD FOR ENZYMATICALLY SYNTHESIZING CYCLIC DI-GMP

(71) Applicant: Yamasa Corporation, Choshi-shi (CH)

(72) Inventors: Kaori Tanabe, Choshi (JP); Kazuya Ishige, Choshi (JP)

(73) Assignee: Yamasa Corporation, Choshi-shi, Chiba (JP)

( * ) Notice: Subject to any disclaimer, the term of this patent is extended or adjusted under 35 U.S.C. 154(b) by 0 days.

(21) Appl. No.: 14/380,873

(22) PCT Filed: Feb. 26, 2013

(86) PCT No.: PCT/JP2013/055018
§ 371 (c)(1),
(2) Date: Aug. 25, 2014

(87) PCT Pub. No.: WO2013/129427
PCT Pub. Date: Sep. 6, 2013

(65) Prior Publication Data
US 2015/0044724 A1 Feb. 12, 2015

(30) Foreign Application Priority Data
Feb. 29, 2012 (JP) .................. 2012-043688

(51) Int. Cl.
*C12N 9/12* (2006.01)
*C12P 19/36* (2006.01)

(52) U.S. Cl.
CPC ............ *C12N 9/1241* (2013.01); *C12P 19/36* (2013.01); *C12Y 207/07065* (2013.01); *C07K 2319/00* (2013.01)

(58) Field of Classification Search
CPC .................................. C12N 9/12; C12P 19/38
See application file for complete search history.

(56) References Cited

U.S. PATENT DOCUMENTS

2012/0040403 A1* 2/2012 Liang .................. C07H 19/20
435/90

FOREIGN PATENT DOCUMENTS

WO WO-2010/066666 A1 6/2010
WO WO-2010/101526 A1 9/2010

OTHER PUBLICATIONS

MW of SEQ ID No. 2 in Liang (last viewed on Nov. 30, 2015).*
A5ILZ5 (last viewed on Apr. 15, 2016).*
A5ILZ5 molecular weight (last viewed on Apr. 15, 2016).*
(Continued)

*Primary Examiner* — Alexander Kim
(74) *Attorney, Agent, or Firm* — Clark & Elbing LLP; Susan M. Michaud

(57) ABSTRACT

A practical method for enzymatically synthesizing c-di-GMP with excellent productivity is provided. A diguanylate cyclase having physical and chemical characteristics (A) to (F): (A) catalytic action on reaction "2 GTP→c-di-GMP"; (B) a molecular weight of 19800±2000; (C) an optimum pH of 7.3 to 9.4; (D) an optimum temperature of 35 to 60° C.; (E) thermal stability as the remaining activity of 90% or higher after heated for 60 minutes under conditions of 50° C. and pH7.8; and (F) the presence of GGDEF (SEQ ID NO:26) domain and the lack of amino acid sequence KXXD (SEQ ID NO:23) in the i-site.

10 Claims, 6 Drawing Sheets

(56) References Cited

OTHER PUBLICATIONS

Takahata et al., *Thermotoga petrophila* sp. nov. and *Thermotoga naphthophila* sp. nov., two hyperthermophilic bacteria from the Kubiki oil reservoir in Niigata, Japan., Int J Syst Evol Microbiol, Sep. 2001, vol. 51, pp. 1901-1909.*

Branden and Tooze, Introduction to Protein Structure (1999), 2nd edition, Garland Science Publisher, pp. 3-12.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Weber et al. Cyclic-di-GMP-mediated signalling within the σS network of *Escherichia coli*, Molecular Microbiology (2006), vol. 62(4), pp. 1014-1034, renumbered as pp. 1-21.*

Korovashkina et al., "Enzymatic synthesis of c-di-GMP using inclusion bodies of Thermotoga maritima full-length diguanylate cyclase," J Biotechnol. 164(2):276-80 (2012).

Seshasayee et al., "Comparative genomics of cyclic-di-GMP signalling in bacteria: post-translational regulation and catalytic activity," Nucleic Acids Res. 38(18):5970-81 (2010).

Spehr et al., "Large-scale production of the immunomodulator c-di-GMP from GMP and ATP by an enzymatic cascade," Appl Biochem Biotechnol. 165(3-4):761-75 (2011).

UniProt Database Accession No. 08W213. Retrieved on Nov. 26, 2015 (1 page).

Yang et al., "The structure and inhibition of a GGDEF diguanylate cyclase complexed with (c-di-GMP)(2) at the active site," Acta Crystallogr D Biol Crystallogr. 67(Pt 12):997-1008 (2011).

Extended European Search Report for European Patent Application No. 13755675.9, dated Dec. 16, 2015 (10 pages).

Christen et al., "Allosteric control of cyclic di-GMP signaling," J Biol Chem. 281(42):32015-24 (2006).

GenBank: CP002442.1, *Geobacillus* sp. Y412MC52, complete genome, uploaded Nov. 21, 2011 (retrieved on Apr. 2, 2013) (2 pages).

Ishige, Kazuya, "Practical enzymatic production of cyclic di-GMP, Development of Cyclic di-GMP mass production technology," Bioscience & Industry. 70(6):466-7 (2012). English translation provided (3 pages).

Rao et al., "Enzymatic synthesis of c-di-GMP using a thermophilic diguanylate cyclase," Anal Biochem. 389(2):138-142 (2009).

Tanabe et al., "Enzymatic synthesis of cyclic di-GMP with high efficiency was conjugated GTP supply system," Japan Society for Bioscience, Biotechnology, and Agrochemistry. Abstract No. 2C29p08, p. 119, Mar. 5, 2011. English translation provided (2 pages).

International Search Report for PCT/JP2013/055018, mailed Apr. 16, 2013 (2 pages).

* cited by examiner

SEQUENCE LISTING

```
<160> NUMBER OF SEQ ID NOS: 27

<210> SEQ ID NO 1
<211> LENGTH: 522
<212> TYPE: DNA
<213> ORGANISM: Geobacillus stearothermophilus

<400> SEQUENCE: 1
atggaccact tcgaaaaaat ggcctacacc gactttttga ccggcatcca taaccgcgcc      60
tacatggatc aaacgatcgc caagctaaac ggatccggtg aatggattgg cgtcgtcgtc     120
gccgatatcg acaattttaa aacgatcaac gacacgtata accatgccgt cggcgacgag     180
gtgatccgcc atttcgcctc aaccttgaaa cagtttctca aagagggcga ttttttgttc     240
```

```
cgcagcggcg gtgaagaatt tacgatgttt ttgcgtaatc gcacatttga agagagcgtc    300
cggcttgtcg aggagattcg agaagcagtg cgccatagca ctgtgttggt cgattatatg    360
gcggcaaaac gtcccattgc ctatacgtcg tcgttcggtc tttactttg tcaagcagaa     420 ggaacgatgt caattgaaaa agcgtacatt tatgccgacc atttattgct ccgttcgaaa    480
gaaagcggca aaataaagt atcagcccaa tgcgggctcg ag                        522
```

<210> SEQ ID NO 2
<211> LENGTH: 174
<212> TYPE: PRT
<213> ORGANISM: Geobacillus stearothermophilus

<400> SEQUENCE: 2

```
Met Asp His Phe Glu Lys Met Ala Tyr Thr Asp Phe Leu Thr Gly Ile
1               5                   10                  15

His Asn Arg Ala Tyr Met Asp Gln Thr Ile Ala Lys Leu Asn Gly Ser
            20                  25                  30

Gly Glu Trp Ile Gly Val Val Ala Asp Ile Asp Asn Phe Lys Thr
        35                  40                  45

Ile Asn Asp Thr Tyr Asn His Ala Val Gly Asp Glu Val Ile Arg His
50                  55                  60

Phe Ala Ser Thr Leu Lys Gln Phe Leu Lys Glu Gly Asp Phe Leu Phe
65                  70                  75                  80

Arg Ser Gly Gly Glu Glu Phe Thr Met Phe Leu Arg Asn Arg Thr Phe
                85                  90                  95

Glu Glu Ser Val Arg Leu Val Glu Ile Arg Glu Ala Val Arg His
            100                 105                 110

Ser Thr Val Leu Val Asp Tyr Met Ala Ala Lys Arg Pro Ile Ala Tyr
        115                 120                 125

Thr Ser Ser Phe Gly Leu Tyr Phe Cys Gln Ala Glu Gly Thr Met Ser
130                 135                 140

Ile Glu Lys Ala Tyr Ile Tyr Ala Asp His Leu Leu Leu Arg Ser Lys
145                 150                 155                 160

Glu Ser Gly Lys Asn Lys Val Ser Ala Gln Cys Gly Leu Glu
                165                 170
```

<210> SEQ ID NO 3
<211> LENGTH: 522
<212> TYPE: DNA
<213> ORGANISM: Geobacillus stearothermophilus

<400> SEQUENCE: 3

```
atggaccact tcgaaaaaat ggcctacacc gactttttga ccggcatcca taaccgcgcc     60
tacatggatc aaacgatcgc caagctaaac ggatccggtg aatggattgg cgtcgtcgtc    120
gccgatatcg acaattttaa aacgatcaac gacacgtata accatgccgt cggcgacgag    180
gtgatccgcc atttcgcctc aaccttgaaa cagtttctcg cagagggcga attcttgttc    240
cgcagcggcg gtgaagaatt tacgatgttt ttgcgtaatc gcacatttga agagagcgtc    300
cggcttgtcg aggagattcg agaagcagtg cgccatagca ctgtgttggt cgattatatg    360
gcggcaaaac gtcccattgc ctatacgtcg tcgttcggtc tttactttg tcaagcagaa     420 ggaacgatgt caattgaaaa agcgtacatt tatgccgacc atttattgct ccgttcgaaa    480
gaaagcggca aaataaagt atcagcccaa tgcgggctcg ag                        522
```

<210> SEQ ID NO 4

```
<211> LENGTH: 174
<212> TYPE: PRT
<213> ORGANISM: Geobacillus stearothermophilus

<400> SEQUENCE: 4
```

| | | | | | | | | | | | | | | | |
|---|---|---|---|---|---|---|---|---|---|---|---|---|---|---|---|
| Met | Asp | His | Phe | Glu | Lys | Met | Ala | Tyr | Thr | Asp | Phe | Leu | Thr | Gly | Ile |
| 1 | | | | 5 | | | | | 10 | | | | | 15 | |
| His | Asn | Arg | Ala | Tyr | Met | Asp | Gln | Thr | Ile | Ala | Lys | Leu | Asn | Gly | Ser |
| | | | 20 | | | | | 25 | | | | | 30 | | |
| Gly | Glu | Trp | Ile | Gly | Val | Val | Ala | Asp | Ile | Asp | Asn | Phe | Lys | Thr | |
| | | 35 | | | | | 40 | | | | | 45 | | | |
| Ile | Asn | Asp | Thr | Tyr | Asn | His | Ala | Val | Gly | Asp | Glu | Val | Ile | Arg | His |
| 50 | | | | | 55 | | | | | 60 | | | | | |
| Phe | Ala | Ser | Thr | Leu | Lys | Gln | Phe | Leu | Ala | Glu | Gly | Glu | Phe | Leu | Phe |
| 65 | | | | | 70 | | | | | 75 | | | | | 80 |
| Arg | Ser | Gly | Gly | Glu | Glu | Phe | Thr | Met | Phe | Leu | Arg | Asn | Arg | Thr | Phe |
| | | | | 85 | | | | | 90 | | | | | 95 | |
| Glu | Glu | Ser | Val | Arg | Leu | Val | Glu | Ile | Arg | Glu | Ala | Val | Arg | His | |
| | | | 100 | | | | | 105 | | | | | 110 | | |
| Ser | Thr | Val | Leu | Val | Asp | Tyr | Met | Ala | Ala | Lys | Arg | Pro | Ile | Ala | Tyr |
| | | 115 | | | | | 120 | | | | | 125 | | | |
| Thr | Ser | Ser | Phe | Gly | Leu | Tyr | Phe | Cys | Gln | Ala | Glu | Gly | Thr | Met | Ser |
| 130 | | | | | 135 | | | | | 140 | | | | | |
| Ile | Glu | Lys | Ala | Tyr | Ile | Tyr | Ala | Asp | His | Leu | Leu | Leu | Arg | Ser | Lys |
| 145 | | | | | 150 | | | | | 155 | | | | | 160 |
| Glu | Ser | Gly | Lys | Asn | Lys | Val | Ser | Ala | Gln | Cys | Gly | Leu | Glu | | |
| | | | | 165 | | | | | 170 | | | | | | |

```
<210> SEQ ID NO 5
<211> LENGTH: 522
<212> TYPE: DNA
<213> ORGANISM: Geobacillus stearothermophilus

<400> SEQUENCE: 5
```

| | | |
|---|---|---|
| atggaccact tcgaaaaaat ggcctacacc gacttttga ccggcatcca taaccgcgcc | 60 |
| tacatggatc aaacgatcgc caagctaaac ggatccggtg aatggattgg cgtcgtcgtc | 120 |
| gccgatatcg acaattttaa acgatcaac gacacgtatg ccatgccgt cggcgacgag | 180 |
| gtgatccgcc atttcgcctc aaccttgaaa cagtttctcg cagagggcga attcttgttc | 240 |
| cgcagcggcg gtgaagaatt tacgatgttt ttgcgtaatc gcacatttga agagagcgtc | 300 |
| cggcttgtcg aggagattcg agaagcagtg cgccatagca ctgtgttggt cgattatatg | 360 |
| gcggcaaaac gtcccattgc ctatacgtcg tcgttcggtc tttactttg tcaagcagaa | 420 |
| ggaacgatgt caattgaaaa agcgtacatt tatgccgacc attattgct ccgttcgaaa | 480 |
| gaaagcggca aaataaagt atcagcccaa tgcgggctcg ag | 522 |

```
<210> SEQ ID NO 6
<211> LENGTH: 174
<212> TYPE: PRT
<213> ORGANISM: Geobacillus stearothermophilus

<400> SEQUENCE: 6
```

| | | | | | | | | | | | | | | | |
|---|---|---|---|---|---|---|---|---|---|---|---|---|---|---|---|
| Met | Asp | His | Phe | Glu | Lys | Met | Ala | Tyr | Thr | Asp | Phe | Leu | Thr | Gly | Ile |
| 1 | | | | 5 | | | | | 10 | | | | | 15 | |
| His | Asn | Arg | Ala | Tyr | Met | Asp | Gln | Thr | Ile | Ala | Lys | Leu | Asn | Gly | Ser |
| | | | 20 | | | | | 25 | | | | | 30 | | |

```
Gly Glu Trp Ile Gly Val Val Ala Asp Ile Asp Asn Phe Lys Thr
            35                  40                  45
Ile Asn Asp Thr Tyr Gly His Ala Val Gly Asp Glu Val Ile Arg His
 50                  55                  60
Phe Ala Ser Thr Leu Lys Gln Phe Leu Ala Glu Gly Glu Phe Leu Phe
 65                  70                  75                  80
Arg Ser Gly Gly Glu Glu Phe Thr Met Phe Leu Arg Asn Arg Thr Phe
                 85                  90                  95
Glu Glu Ser Val Arg Leu Val Glu Glu Ile Arg Glu Ala Val Arg His
                100                 105                 110
Ser Thr Val Leu Val Asp Tyr Met Ala Ala Lys Arg Pro Ile Ala Tyr
                115                 120                 125
Thr Ser Ser Phe Gly Leu Tyr Phe Cys Gln Ala Glu Gly Thr Met Ser
            130                 135                 140
Ile Glu Lys Ala Tyr Ile Tyr Ala Asp His Leu Leu Leu Arg Ser Lys
145                 150                 155                 160
Glu Ser Gly Lys Asn Lys Val Ser Ala Gln Cys Gly Leu Glu
                165                 170
```

<210> SEQ ID NO 7
<211> LENGTH: 1416
<212> TYPE: DNA
<213> ORGANISM: Geobacillus stearothermophilus

<400> SEQUENCE: 7

```
atggcctaca ctaccagaca aattggtgcc aagaacacct tggaatacaa agtttatatc      60
gaaaaggatg gtaagccagt ttctgccttc cacgacattc ccttgtacgc tgacaaggaa     120
aacaacattt tcaacatggt tgttgaaatt ccacgttgga ccaacgccaa gttagaaatc     180
accaaggaag aaactttgaa cccaatcatc caagacacca gaagggcaa gttgagattt     240
gttagaaact gtttccctca tcatggttac attcacaact atggtgcttt cccacaaact     300
tgggaagacc caaacgtaag ccacccagaa actaaggcag ttggtgacaa cgatccaatt     360
gatgtgttgg aaattggtga actattgct tacactggtc aagtcaagca agttaaggct     420
ctaggtatca tggctttatt ggatgaaggt gagaccgatt ggaaagttat tgccattgat     480
attaacgatc cattagcccc aaaattgaac gacattgagg atgttgagaa atacttccca     540
ggtctgttga gggctactaa cgaatggttc agaattaca aaatcccaga tggtaagcca     600
gaaaaccaat tgcctctc cggtgaagct aagaacaaga gtacgctttt ggatatcatc     660
aaggaaacac atgactcctg aaacaattaa attgctggta agtcttctga cagcaagggt     720
attgatttga ccaatgttac tttgcctgac accccaacct actccaaggc tgcctctgat     780
gccatcccac cagcttctcc aaaggcagat gctccaattg acaagtctat tgacaagtgg     840
ttcttcatct ccggttctgt tgagctcggt ggcggtggct cgggcggtgg tgggtcggac     900
cacttcgaaa aaatggccta caccgacttt tgaccggca tccataaccg cgcctacatg     960
gatcaaacga tcgccaagct aaacggatcc ggtgaatgga ttggcgtcgt cgtcgccgat    1020
atcgacaatt ttaaaacgat caacgacacg tataaccatg ccgtcggcga cgaggtgatc    1080
cgccatttcg cctcaacctt gaaacagttt ctcgcagagg gcgaattctt gttccgcagc    1140
ggcggtgaag aatttacgat gtttttgcgt aatcgcacat tgaagagag cgtccggctt    1200
gtcgaggaga ttcgagaagc agtgcgccat agcactgtgt tggtcgatta tatggcggca    1260
aaacgtccca ttgcctatac gtcgtcgttc ggtctttact tttgtcaagc agaaggaacg    1320
```

```
atgtcaattg aaaaagcgta catttatgcc gaccatttat tgctccgttc gaaagaaagc   1380
ggcaaaaata agtatcagc ccaatgcggg ctcgag                              1416
```

<210> SEQ ID NO 8
<211> LENGTH: 472
<212> TYPE: PRT
<213> ORGANISM: Geobacillus stearothermophilus

<400> SEQUENCE: 8

```
Met Ala Tyr Thr Thr Arg Gln Ile Gly Ala Lys Asn Thr Leu Glu Tyr
 1               5                  10                  15

Lys Val Tyr Ile Glu Lys Asp Gly Lys Pro Val Ser Ala Phe His Asp
            20                  25                  30

Ile Pro Leu Tyr Ala Asp Lys Glu Asn Asn Ile Phe Asn Met Val Val
        35                  40                  45

Glu Ile Pro Arg Trp Thr Asn Ala Lys Leu Glu Ile Thr Lys Glu Glu
    50                  55                  60

Thr Leu Asn Pro Ile Ile Gln Asp Thr Lys Lys Gly Lys Leu Arg Phe
65                  70                  75                  80

Val Arg Asn Cys Phe Pro His His Gly Tyr Ile His Asn Tyr Gly Ala
                85                  90                  95

Phe Pro Gln Thr Trp Glu Asp Pro Asn Val Ser His Pro Glu Thr Lys
           100                 105                 110

Ala Val Gly Asp Asn Asp Pro Ile Asp Val Leu Glu Ile Gly Glu Thr
       115                 120                 125

Ile Ala Tyr Thr Gly Gln Val Lys Gln Val Lys Ala Leu Gly Ile Met
   130                 135                 140

Ala Leu Leu Asp Glu Gly Glu Thr Asp Trp Lys Val Ile Ala Ile Asp
145                 150                 155                 160

Ile Asn Asp Pro Leu Ala Pro Lys Leu Asn Asp Ile Glu Asp Val Glu
                165                 170                 175

Lys Tyr Phe Pro Gly Leu Leu Arg Ala Thr Asn Glu Trp Phe Arg Ile
           180                 185                 190

Tyr Lys Ile Pro Asp Gly Lys Pro Glu Asn Gln Phe Ala Phe Ser Gly
       195                 200                 205

Glu Ala Lys Asn Lys Lys Tyr Ala Leu Asp Ile Ile Lys Glu Thr His
   210                 215                 220

Asp Ser Trp Lys Gln Leu Ile Ala Gly Lys Ser Ser Asp Ser Lys Gly
225                 230                 235                 240

Ile Asp Leu Thr Asn Val Thr Leu Pro Asp Thr Pro Thr Tyr Ser Lys
                245                 250                 255

Ala Ala Ser Asp Ala Ile Pro Pro Ala Ser Pro Lys Ala Asp Ala Pro
           260                 265                 270

Ile Asp Lys Ser Ile Asp Lys Trp Phe Phe Ile Ser Gly Ser Val Glu
       275                 280                 285

Leu Gly Gly Gly Ser Gly Gly Gly Ser Asp His Phe Glu Lys
   290                 295                 300

Met Ala Tyr Thr Asp Phe Leu Thr Gly Ile His Asn Arg Ala Tyr Met
305                 310                 315                 320

Asp Gln Thr Ile Ala Lys Leu Asn Gly Ser Gly Glu Trp Ile Gly Val
                325                 330                 335

Val Val Ala Asp Ile Asp Asn Phe Lys Thr Ile Asn Asp Thr Tyr Asn
           340                 345                 350

His Ala Val Gly Asp Glu Val Ile Arg His Phe Ala Ser Thr Leu Lys
```

|  | 355 |  |  |  | 360 |  |  |  | 365 |  |  |
|---|---|---|---|---|---|---|---|---|---|---|---|

Gln Phe Leu Ala Glu Gly Glu Phe Leu Phe Arg Ser Gly Gly Glu Glu
   370                 375                 380

Phe Thr Met Phe Leu Arg Asn Arg Thr Phe Glu Glu Ser Val Arg Leu
385                 390                 395                 400

Val Glu Glu Ile Arg Glu Ala Val Arg His Ser Thr Val Leu Val Asp
            405                 410                 415

Tyr Met Ala Ala Lys Arg Pro Ile Ala Tyr Thr Ser Ser Phe Gly Leu
        420                 425                 430

Tyr Phe Cys Gln Ala Glu Gly Thr Met Ser Ile Glu Lys Ala Tyr Ile
    435                 440                 445

Tyr Ala Asp His Leu Leu Leu Arg Ser Lys Glu Ser Gly Lys Asn Lys
450                 455                 460

Val Ser Ala Gln Cys Gly Leu Glu
465                 470

<210> SEQ ID NO 9
<211> LENGTH: 1416
<212> TYPE: DNA
<213> ORGANISM: Geobacillus stearothermophilus

<400> SEQUENCE: 9

| atggcctaca | ctaccagaca | aattggtgcc | aagaacacct | tggaatacaa | agtttatatc | 60 |
|---|---|---|---|---|---|---|
| gaaaaggatg | gtaagccagt | ttctgccttc | cacgacattc | ccttgtacgc | tgacaaggaa | 120 |
| aacaacattt | tcaacatggt | tgttgaaatt | ccacgttgga | ccaacgccaa | gttagaaatc | 180 |
| accaaggaag | aaactttgaa | cccaatcatc | caagacacca | agaagggcaa | gttgagattt | 240 |
| gttagaaact | gtttccctca | tcatggttac | attcacaact | atggtgcttt | cccacaaact | 300 |
| tgggaagacc | caaacgtaag | ccacccagaa | actaaggcag | ttggtgacaa | cgatccaatt | 360 |
| gatgtgttgg | aaattggtga | actattgct | tacactggtc | aagtcaagca | agttaaggct | 420 |
| ctaggtatca | tggctttatt | ggatgaaggt | gagaccgatt | ggaaagttat | tgccattgat | 480 |
| attaacgatc | cattagcccc | aaaattgaac | gacattgagg | atgttgagaa | atacttccca | 540 |
| ggtctgttga | gggctactaa | cgaatggttc | agaatttaca | aaatcccaga | tggtaagcca | 600 |
| gaaaaccaat | ttgccttctc | cggtgaagct | aagaacaaga | agtacgcttt | ggatatcatc | 660 |
| aaggaaacac | atgactcctg | aaacaattta | attgctggta | agtcttctga | cagcaagggt | 720 |
| attgatttga | ccaatgttac | tttgcctgac | accccaacct | actccaaggc | tgcctctgat | 780 |
| gccatcccac | cagcttctcc | aaaggcagat | gctccaattg | acaagtctat | tgacaagtgg | 840 |
| ttcttcatct | ccggttctgt | tgagctcggt | ggcggtggct | cgggcggtgg | tgggtcggac | 900 |
| cacttcgaaa | aaatggccta | caccgacttt | ttgaccggca | tccataaccg | cgcctacatg | 960 |
| gatcaaacga | tcgccaagct | aaacggatcc | ggtgaatgga | ttggcgtcgt | cgtcgccgat | 1020 |
| atcgacaatt | ttaaaacgat | caacgacacg | tatggccatg | ccgtcggcga | cgaggtgatc | 1080 |
| cgccatttcg | cctcaacctt | gaaacagttt | ctcgcagagg | gcgaattctt | gttccgcagc | 1140 |
| ggcggtgaag | aatttacgat | gtttttgcgt | aatcgcacat | tgaagagag | cgtccggctt | 1200 |
| gtcgaggaga | ttcgagaagc | agtgcgccat | agcactgtgt | tggtcgatta | tatggcggca | 1260 |
| aaacgtccca | ttgcctatac | gtcgtcgttc | ggtctttact | tttgtcaagc | agaaggaacg | 1320 |
| atgtcaattg | aaaagcgta | catttatgcc | gaccatttat | tgctccgttc | gaaagaaagc | 1380 |
| ggcaaaaata | agtatcagc | ccaatgcggg | ctcgag |  |  | 1416 |

<210> SEQ ID NO 10
<211> LENGTH: 472
<212> TYPE: PRT
<213> ORGANISM: Geobacillus stearothermophilus

<400> SEQUENCE: 10

```
Met Ala Tyr Thr Thr Arg Gln Ile Gly Ala Lys Asn Thr Leu Glu Tyr
1               5                   10                  15
Lys Val Tyr Ile Glu Lys Asp Gly Lys Pro Val Ser Ala Phe His Asp
            20                  25                  30
Ile Pro Leu Tyr Ala Asp Lys Glu Asn Asn Ile Phe Asn Met Val Val
        35                  40                  45
Glu Ile Pro Arg Trp Thr Asn Ala Lys Leu Glu Ile Thr Lys Glu Glu
    50                  55                  60
Thr Leu Asn Pro Ile Ile Gln Asp Thr Lys Lys Gly Lys Leu Arg Phe
65                  70                  75                  80
Val Arg Asn Cys Phe Pro His His Gly Tyr Ile His Asn Tyr Gly Ala
                85                  90                  95
Phe Pro Gln Thr Trp Glu Asp Pro Asn Val Ser His Pro Glu Thr Lys
            100                 105                 110
Ala Val Gly Asp Asn Asp Pro Ile Asp Val Leu Glu Ile Gly Glu Thr
        115                 120                 125
Ile Ala Tyr Thr Gly Gln Val Lys Gln Val Lys Ala Leu Gly Ile Met
    130                 135                 140
Ala Leu Leu Asp Glu Gly Glu Thr Asp Trp Lys Val Ile Ala Ile Asp
145                 150                 155                 160
Ile Asn Asp Pro Leu Ala Pro Lys Leu Asn Asp Ile Glu Asp Val Glu
                165                 170                 175
Lys Tyr Phe Pro Gly Leu Leu Arg Ala Thr Asn Glu Trp Phe Arg Ile
            180                 185                 190
Tyr Lys Ile Pro Asp Gly Lys Pro Glu Asn Gln Phe Ala Phe Ser Gly
        195                 200                 205
Glu Ala Lys Asn Lys Lys Tyr Ala Leu Asp Ile Ile Lys Glu Thr His
    210                 215                 220
Asp Ser Trp Lys Gln Leu Ile Ala Gly Lys Ser Ser Asp Ser Lys Gly
225                 230                 235                 240
Ile Asp Leu Thr Asn Val Thr Leu Pro Asp Thr Pro Thr Tyr Ser Lys
                245                 250                 255
Ala Ala Ser Asp Ala Ile Pro Pro Ala Ser Pro Lys Ala Asp Ala Pro
            260                 265                 270
Ile Asp Lys Ser Ile Asp Lys Trp Phe Phe Ile Ser Gly Ser Val Glu
        275                 280                 285
Leu Gly Gly Gly Gly Ser Gly Gly Gly Ser Asp His Phe Glu Lys
    290                 295                 300
Met Ala Tyr Thr Asp Phe Leu Thr Gly Ile His Asn Arg Ala Tyr Met
305                 310                 315                 320
Asp Gln Thr Ile Ala Lys Leu Asn Gly Ser Gly Glu Trp Ile Gly Val
                325                 330                 335
Val Val Asp Ile Asp Asn Phe Lys Thr Ile Asn Asp Thr Tyr Gly
            340                 345                 350
His Ala Val Gly Asp Glu Val Ile Arg His Phe Ala Ser Thr Leu Lys
        355                 360                 365
Gln Phe Leu Ala Glu Gly Glu Phe Leu Phe Arg Ser Gly Gly Glu Glu
    370                 375                 380
```

Phe Thr Met Phe Leu Arg Asn Arg Thr Phe Glu Glu Ser Val Arg Leu
385                 390                 395                 400

Val Glu Glu Ile Arg Glu Ala Val Arg His Ser Thr Val Leu Val Asp
            405                 410                 415

Tyr Met Ala Ala Lys Arg Pro Ile Ala Tyr Thr Ser Ser Phe Gly Leu
        420                 425                 430

Tyr Phe Cys Gln Ala Glu Gly Thr Met Ser Ile Glu Lys Ala Tyr Ile
    435                 440                 445

Tyr Ala Asp His Leu Leu Leu Arg Ser Lys Gly Ser Gly Lys Asn Lys
450                 455                 460

Val Ser Ala Gln Cys Gly Leu Glu
465                 470

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
aaccatggga ctccgagcac gaccgattat                                    30

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
aaactcgagc ccgcattggg ctgatac                                       27

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
gtttctcgca gagggcgaat tcttgttccg cagcgg                             36

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14
cgccctctgc gagaaactgt ttcaaggttg ag                                 32

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
cacgtatggc catgccgtcg gcgacga                                       27

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
cggcatggcc atacgtgtcg ttgatcgttt taaa            34

<210> SEQ ID NO 17
<211> LENGTH: 58
<212> TYPE: DNA
<213> ORGANISM: Artificial Sequence
<220> FEATURE:
<223> OTHER INFORMATION: Primer

<400> SEQUENCE: 17
aagagctcgg tggcggtggc tcgggcggtg gtgggtcgga ccacttcgaa aaaatggc            58

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
aaactcgagc ccgcattggg ctgatac            27

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
catgccatgg cctacactac cagacaaa            28

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
gttagaaact gtttccctca tcatggttac attcacaact            40

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
aaccatgatg agggaaacag tttctaac            28

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
ttgagctcaa cagaaccgga gatgaagaac c                              31

<210> SEQ ID NO 23
<211> LENGTH: 4
<212> TYPE: PRT
<213> ORGANISM: Geobacillus stearothermophilus
<220> FEATURE:
<221> NAME/KEY: MISC_FEATURE
<222> LOCATION: (2)..(3)
<223> OTHER INFORMATION: Xaa is any amino acid

<400> SEQUENCE: 23

Lys Xaa Xaa Asp
1

<210> SEQ ID NO 24
<211> LENGTH: 1239
<212> TYPE: DNA
<213> ORGANISM: Geobacillus stearothermophilus

<400> SEQUENCE: 24

| | |
|---|---|
| atgttactcc gagcacgacc gatgattttt gctgtttttt ccgcatccat tgttgttgtt | 60 |
| tttgtgtcag aaccgccttc cttcgatcgc acctatgtca tcgctttgct gttttattgg | 120 |
| ctgttttcca gcttgtattc acacttgcgc gtcatagaca aaacgaaaaa caatattccc | 180 |
| gttgattacg gcattaacta tagtttatcg ttcgccttat tgccggcccc gttcgggctg | 240 |
| tttatctttg aagcgttgtt tcgcttgact gaacatatag caaaaaaata tttgaaaaca | 300 |
| gcggaacccg atgaatggct gcacacattg tacaacatcg gctcgtttgt gacgttcaat | 360 |
| tcgctcgcgt ttgccttata caatctcctt ggtccgctgt tcagtctat tccgttcatt | 420 |
| ggcttctggc tgcttttatt cctgctcgtc atcgtcgttt ccttttttgac tgactgttgc | 480 |
| ctgatcatca ttttttatat aaccggcgac attcagacac agcgcgaggc gttggatttt | 540 |
| attaagacga gaagctggat ggacatggga aaaacggcgc tgacaaacgg tctgttatt | 600 |
| ctcttttgc aagaacagcg gtgggatatg cttttgagct tatttttgct gaattacttc | 660 |
| gtcagccgct cgttcttttc caaatcgcaa agcatccagc ataaactaga acgcgaccac | 720 |
| ttcgaaaaaa tggcctacac cgactttttg accggcatcc ataaccgcgc ctacatggat | 780 |
| caaacgatcg ccaagctaaa cggatccggt gaatggattg gcgtcgtcgt cgccgatatc | 840 |
| gacaattta aaacgatcaa cgacacgtat aaccatgccg tcggcgacga ggtgatccgc | 900 |
| catttcgcct caaccttgaa acagtttctc aaagagggcg attttttgtt ccgcagcggc | 960 |
| ggtgaagaat ttacgatgtt tttgcgtaat cgcacatttg aagagagcgt ccggcttgtc | 1020 |
| gaggagattc gagaagcagt gcgccatagc actgtgttgg tcgattatat ggcggcaaaa | 1080 |
| cgtcccattg cctatacgtc gtcgttcggt ctttactttt gtcaagcaga aggaacgatg | 1140 |
| tcaattgaaa aagcgtacat ttatgccgac catttattgc tccgttcgaa agaaagcggc | 1200 |
| aaaaataaag tatcagccca atgcggggga gttgcataa | 1239 |

<210> SEQ ID NO 25
<211> LENGTH: 412
<212> TYPE: PRT
<213> ORGANISM: Geobacillus stearothermophilus

<400> SEQUENCE: 25

Met Leu Leu Arg Ala Arg Pro Met Ile Phe Ala Val Phe Ser Ala Ser

```
  1               5                  10                 15
Ile Val Val Phe Val Ser Glu Pro Pro Ser Phe Asp Arg Thr Tyr
             20                 25                 30
Val Ile Ala Leu Leu Phe Tyr Trp Leu Phe Ser Ser Leu Tyr Ser His
             35                 40                 45
Leu Arg Val Ile Asp Lys Thr Lys Asn Asn Ile Pro Val Asp Tyr Gly
 50                 55                 60
Ile Asn Tyr Ser Leu Ser Phe Ala Leu Phe Ala Gly Pro Phe Gly Leu
 65                 70                 75                 80
Phe Ile Phe Glu Ala Leu Phe Arg Leu Thr Glu His Ile Ala Lys Lys
                 85                 90                 95
Tyr Leu Lys Thr Ala Glu Pro Asp Glu Trp Leu His Thr Leu Tyr Asn
                100                105                110
Ile Gly Ser Phe Val Thr Phe Asn Ser Leu Ala Phe Ala Leu Tyr Asn
                115                120                125
Leu Leu Gly Pro Leu Phe Gln Ser Ile Pro Phe Ile Gly Phe Trp Leu
130                135                140
Leu Leu Phe Leu Leu Val Ile Val Ser Phe Leu Thr Asp Cys Cys
145                150                155                160
Leu Ile Ile Ile Phe Tyr Ile Thr Gly Asp Ile Gln Thr Gln Arg Glu
                165                170                175
Ala Leu Asp Phe Ile Lys Thr Arg Ser Trp Met Asp Met Gly Lys Thr
                180                185                190
Ala Leu Thr Asn Gly Leu Leu Phe Leu Phe Leu Gln Glu Gln Arg Trp
                195                200                205
Asp Met Leu Leu Ser Leu Phe Leu Leu Asn Tyr Phe Val Ser Arg Ser
                210                215                220
Phe Phe Ser Lys Ser Gln Ser Ile Gln His Lys Leu Glu Arg Asp His
225                230                235                240
Phe Glu Lys Met Ala Tyr Thr Asp Phe Leu Thr Gly Ile His Asn Arg
                245                250                255
Ala Tyr Met Asp Gln Thr Ile Ala Lys Leu Asn Gly Ser Gly Glu Trp
                260                265                270
Ile Gly Val Val Val Ala Asp Ile Asp Asn Phe Lys Thr Ile Asn Asp
                275                280                285
Thr Tyr Asn His Ala Val Gly Asp Glu Val Ile Arg His Phe Ala Ser
                290                295                300
Thr Leu Lys Gln Phe Leu Lys Glu Gly Asp Phe Leu Phe Arg Ser Gly
305                310                315                320
Gly Glu Glu Phe Thr Met Phe Leu Arg Asn Arg Thr Phe Glu Glu Ser
                325                330                335
Val Arg Leu Val Glu Glu Ile Arg Glu Ala Val Arg His Ser Thr Val
                340                345                350
Leu Val Asp Tyr Met Ala Ala Lys Arg Pro Ile Ala Tyr Thr Ser Ser
                355                360                365
Phe Gly Leu Tyr Phe Cys Gln Ala Glu Gly Thr Met Ser Ile Glu Lys
                370                375                380
Ala Tyr Ile Tyr Ala Asp His Leu Leu Leu Arg Ser Lys Glu Ser Gly
385                390                395                400
Lys Asn Lys Val Ser Ala Gln Cys Gly Gly Val Ala
                405                410

<210> SEQ ID NO 26
```

```
<211> LENGTH: 5
<212> TYPE: PRT
<213> ORGANISM: Geobacillus stearothemophilus

<400> SEQUENCE: 26

Gly Gly Asp Glu Phe
1               5

<210> SEQ ID NO 27
<211> LENGTH: 10
<212> TYPE: PRT
<213> ORGANISM: Artificial Sequence
<220> FEATURE:
<223> OTHER INFORMATION: Linker

<400> SEQUENCE: 27

Gly Gly Gly Gly Ser Gly Gly Gly Gly Ser
1               5                   10
```

PRACTICAL METHOD FOR ENZYMATICALLY SYNTHESIZING CYCLIC DI-GMP

TECHNICAL FIELD

The present invention relates to a novel enzyme with diguanylate cyclase activity and a practical method for synthesizing cyclic di-GMP using the enzyme.

BACKGROUND ART

Cyclic di-GMP (hereinafter, sometimes called "c-di-GMP") is a bacterial signal molecule involved in biofilm formation, motility, virulence factor expression, and the like of bacteria, and the physiological activity, the signaling mechanism, and the like thereof receive attention in recent years. For example, c-di-GMP was found to have immunostimulatory action and is used as an adjuvant, an active ingredient of an allergy-regulating drug, and the like, thereby being recently expected to be promising as a pharmaceutical.

C-di-GMP has been only limitedly available and very expensive. Because of this, in order to produce c-di-GMP efficiently, chemical synthesis and enzymatic synthesis have been conventionally studied and, among these, enzymatic synthesis has been considered to be practical as the production method.

C-di-GMP can be synthesized from two GTP molecules by a two-step enzymatic reaction via the catalytic action of a diguanylate cyclase (hereinafter, sometimes called "DGC"). DGCs derived from various living organisms have "GGDEF (SEQ ID NO:26) domain", which is responsible for the activity and is well conserved among biological species. GGDEF (SEQ ID NO:26) domain has a region called an i-site that is known to be involved in product inhibition in a c-di-GMP synthesis reaction. Various living organisms have a gene that has GGDEF (SEQ ID NO:26) domain and is supposed to have DGC activity. The GGDEF (SEQ ID NO:26) domains have high homology with each other, while the regions other than the GGDEF (SEQ ID NO:26) domains vary to a great extent among the genes and assume different structures.

As a known, conventional method for enzymatically synthesizing c-di-GMP, a one-pot synthesis of c-di-GMP is disclosed where a mutant DGC that is derived from *Caulobacter crescentus* and results from expression in *Escherichia coli* or the like in a large amount in the form of an inclusion body is used along with a guanylate kinase and a nucleoside diphosphate kinase (Patent Document 1). With its c-di-GMP production process requiring a step of purifying an inclusion body from an *Escherichia coli* cell and a step of refolding the resultant DGC in the form of an inclusion body for reactivation, the method in Patent Document 1 has too many complicated treatment processes for large-scale industrial synthesis, thereby having many problems.

As another known method, use of a DGC derived from thermophilic bacterium *Thermotoga maritima* is known (Patent Document 2 and Non-patent Document 1). It is described that synthesis in this method used a modified enzyme obtained by exclusively expressing GGDEF (SEQ ID NO:26) domain, which is the minimum functional region, of a DGC derived from *T. maritima* and, into the i-site, introducing amino acid mutation so as to remove product inhibition.

The inventors of the present invention reported development of a c-di-GMP synthesis system where a DGC derived from *Geobacillus stearothermophilus* (hereinafter, sometimes called "GsDGC") is used (Non-patent Document 2). Non-patent Document 2 describes a combined use of polyphosphate:AMP phosphotransferase derived from *Acinetobacter johnsonii* and a polyphosphate-dependent nucleoside diphosphate kinase derived from *Pseudomonas aeruginosa* in the enzymatic reaction system to develop a system for supplying GTP from GMP provided by polyphosphoric acid serving as a donor. The synthesis system in Non-patent Document 2 does not need frequent GTP addition that is necessary in the synthesis system in Patent Document 2 and Non-patent Document 1 due to substrate inhibition caused by GTP, and is therefore an excellent synthesis system. As GTP is expensive, the synthesis system in Non-patent Document 2 has cost advantage as well.

PRIOR ART DOCUMENT

Patent Document

Patent Literature 1: International Publication No. WO 2010/066666
Patent Literature 2: International Publication No. WO 2010/101526

Non Patent Document

Non Patent Literature 1: Analytical Biochemistry, Vol. 389 p. 138-142 (2009)
Non Patent Literature 2: Abstracts of Presentations at the Annual Meeting of the Japan Society for Bioscience, Biotechnology, and Agrochemistry (2011, Kyoto), p. 119

SUMMARY

Technical Problem

In the method for c-di-GMP production with the use of GsDGC in Non-patent Document 2, however, enzyme activity is not high enough and therefore a significant amount of culture medium for bacterial cells for GsDGC is required relative to the amount of the reaction mixture. In addition, the method has further disadvantages including the necessity of enzyme purification at the time of reaction and complicated procedure and therefore is nowhere near a realistic method for enzymatic synthesis in an industrial scale yet.

As explained in examples below, the inventors of the present invention also attempted gene manipulation described in Patent Document 2 and Non-patent Document 1 by using an enzyme derived from *G. stearothermophilus*. Specifically, GGDEF (SEQ ID NO:26) domain of a DGC derived from *G. stearothermophilus* was exclusively expressed and, into the i-site, amino acid mutation was introduced. This, again, did not give adequate enzyme activity.

The present invention is devised based on the circumstances described above, and an object thereof is to provide a practical method for enzymatically synthesizing c-di-GMP.

Solution to Problem

The inventors of the present invention have conducted intensive research. As a result, they have prepared a novel modified enzyme with specific activity, productivity, and thermal stability remarkably enhanced compared to conventional modified enzymes and have established a system for enzymatically synthesizing c-di-GMP with high efficiency. Thus, the present invention has now been completed.

Specifically, as described in examples below, after the minimum functional region of GsDGC was exclusively expressed and mutation was introduced into the i-site thereof, the resultant modified enzyme (hereinafter, sometimes called "tiGs3466") was subjected to mutagenesis to replace 54th residue asparagine with glycine. The enzyme thus obtained had characteristics that specific activity and enzymatic productivity were remarkably enhanced and thermal stability was extremely high compared to conventional DGCs. The inventors of the present invention found that industrial-scale synthesis of c-di-GMP became more practical and completed the present invention.

The present invention provides:
a diguanylate cyclase with physical and chemical characteristics of:
(A) catalytic action on reaction "2 GTP c-di-GMP";
(B) a molecular weight of 19800±2000;
(C) an optimum pH of 7.3 to 9.4;
(D) an optimum temperature of 35 to 60° C.;
(E) thermal stability as the remaining activity of 90% or higher after heated for 60 minutes under conditions of 50° C. and pH7.8; and
(F) the presence of GGDEF (SEQ ID NO:26) domain and the lack of amino acid sequence KXXD (SEQ ID NO:23) in the i-site.

A DGC with such properties is verified in examples below to be remarkably enhanced in specific activity and enzymatic productivity and have extremely high thermal stability compared to conventional DGCs. This allows industrial-scale synthesis of c-di-GMP to be more practical. Here, GGDEF (SEQ ID NO:26) domain refers to the minimum functional region of a diguanylate cyclase. The i-site refers to a region in GGDEF (SEQ ID NO:26) domain to control product inhibition. The i-site contains a characteristic motif shown under amino acid sequence KXXD (SEQ ID NO:23). X in KXXD (SEQ ID NO:23) denotes any amino acid residue.

The present invention also provides a DGC having one or more amino acid sequences selected from the group consisting of (G) the amino acid sequence shown under SEQ ID NO:6, (H) an amino acid sequence having identity of 90% or higher with the amino acid sequence shown under SEQ ID NO:6, having 54th residue glycine in the amino acid sequence shown under SEQ ID N0:6 conserved, and with the lack of amino acid sequence KXXD (SEQ ID NO:23) in the i-site, (I) an amino acid sequence equivalent to the amino acid sequence shown under SEQ ID NO:6 including deletion, substitution, insertion, or addition of one or several amino acids, having 54th residue glycine in the amino acid sequence shown under SEQ ID NO:6 conserved, and with the lack of amino acid sequence KXXD (SEQ ID NO:23) in the i-site, and (J) an amino acid sequence coded by the base sequence of a nucleic acid that hybridizes, under stringent conditions, with a nucleic acid having a base sequence complementary to a base sequence coding for the amino acid sequence shown under SEQ ID NO:6, having 54th residue glycine in the amino acid sequence shown under SEQ ID NO:6 conserved, and with the lack of amino acid sequence KXXD (SEQ ID NO:23) in the i-site.

The present invention also provides a fusion enzyme resulting from fusion of a dimerizable protein to the N-terminus of the DGC. The present invention also provides a protein fragment of the DGC or of the fusion enzyme, with diguanylate cyclase activity.

The present invention also provides a polynucleotide or an expression vector coding for the DGC, the protein fragment of the fusion enzyme, or the protein fragment. The present invention also provides a transformant resulting from transformation with the polynucleotide or the expression vector.

The present invention also provides a method for producing c-di-GMP from two GTP molecules using an enzyme, wherein the enzyme is a diguanylate cyclase or a fusion enzyme containing a diguanylate cyclase obtained by culturing a transformant resulting from transformation of a host microorganism with the expression vector.

Effects of the Invention

The enzyme of the present invention is remarkably enhanced in specific activity, enzymatic productivity, and thermal stability compared to conventionally known DGCs. Therefore, a method with the use of the enzyme allows extremely efficient synthesis of c-di-GMP compared to conventional enzymatic synthesis. In the synthesis, a crude enzyme solution derived from bacterial cells can be used as it is and the required usage of the enzyme solution is small. Thus, the enzyme of the present invention and a method for c-di-GMP synthesis with the use of the enzyme are extremely useful as a practical method for producing c-di-GMP.

DESCRIPTION OF EMBODIMENTS

Figure 1:
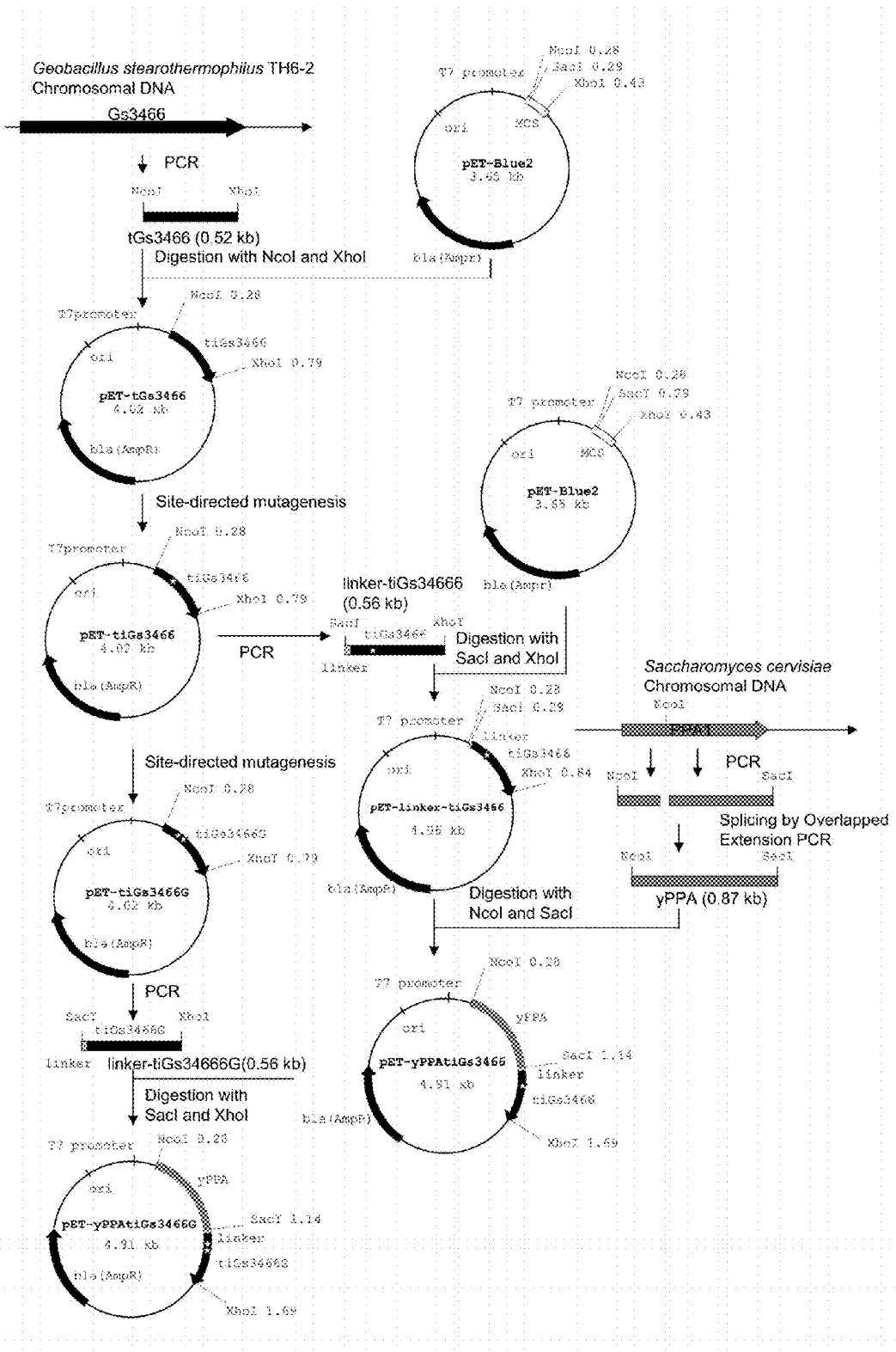
FIG. 1 is a conceptual view of the procedure for preparing various plasmids in examples.

The embodiments of the present invention will be described in detail. An overlapping explanation of the same content is omitted, as needed, to avoid complexity caused by repetition.

(1) Novel DGC

An embodiment of the present invention is a novel DGC. The DGC may have physical and chemical characteristics (A) to (F): (A) catalytic action on reaction "2 GTP c-di-GMP"; (B) a molecular weight of 19800±2000; (C) an optimum pH of 7.3 to 9.4; (D) an optimum temperature of 35 to 60° C.; (E) thermal stability as the remaining activity of 90% or higher after heated for 60 minutes under conditions of 50° C. and pH7.8; and (F) the presence of GGDEF (SEQ ID NO:26) domain and the lack of amino acid sequence KXXD (SEQ ID NO:23) in the i-site. A DGC having characteristics (A) to (F) is verified in examples to have remarkably high specific activity and enzymatic productivity and also have extremely high thermal stability compared to tiGs3466 (a DGC having the amino acid sequence shown under SEQ ID N0:4). Therefore, use of a DGC having such physical and chemical characteristics can make industrial-scale synthesis of c-di-GMP more practical.

A DGC according to an embodiment of the present invention may have the amino acid sequence shown under SEQ ID NO:6. However, the amino acid sequence is not limited to the exact amino acid sequence shown under SEQ ID N0:6 provided that it has mutation of 54th residue asparagine in tiGs3466 to glycine and maintains DGC activity, and may be an amino acid sequence equivalent to the amino acid sequence shown under SEQ ID NO:6 including deletion, substitution, modification, or addition of one or several amino acids. Alternatively, the DGC may be an enzyme having identity of 90% or higher with the amino acid sequence shown under SEQ ID N0:6 provided that it has mutation of 54th residue asparagine in tiGs3466 to glycine and maintains DGC activity. Alternatively, the DGC may be an enzyme having an amino acid sequence coded by the base sequence of a nucleic acid that hybridizes, under stringent conditions, with a nucleic acid having a base sequence complementary to a base sequence coding for the amino acid sequence shown under SEQ ID NO:6 provided that it has mutation of 54th residue asparagine in tiGs3466 to glycine and maintains DGC activity.

A DGC according to an embodiment of the present invention may have mutation in the i-site. Specifically, the amino acid sequence thereof may be lacking in amino acid sequence KXXD (SEQ ID NO:23), for example. As the position of an i-site is well known to those skilled in the art, the sequence of a DGC in question may be compared to the sequence of a DGC derived from *Geobacillus stearothermophilus*, for example, so as to locate the i-site of the DGC in question at the region corresponding to KEGD of the DGC derived from *Geobacillus stearothermophilus*. A DGC according to an embodiment of the present invention may have GGDEF (SEQ ID NO:26) domain. As the sequence of GGDEF (SEQ ID NO:26) domain is well conserved among living organisms, GGDEF (SEQ ID NO:26) domain can be located, as needed, by a search (or comparison) based on the base sequences, the amino acid sequences, and/or the like known for GGDEF (SEQ ID NO:26) domain.

A DGC according to an embodiment of the present invention may be a fusion enzyme comprised of the DGC and a dimerizable protein. For example, it is verified in examples below that a DGC to which a dimerizable inorganic pyrophosphatase is fused is improved in efficiency of c-di-GMP production. The dimerizable protein can be selected by those skilled in the art, and examples thereof include inorganic pyrophosphatases (yPPAs).

A DGC according to an embodiment of the present invention can be obtained by the following method, for example.

(2) Preparation of tiGs3466

(2-1) Cloning of Minimum Functional Region of GsDGC

A gene coding for the minimum functional region of GsDGC (hereinafter, sometimes called "tGs3466 gene") is obtained from *Geobacillus stearothermophilus* to use for preparing a recombinant vector. Cloning is performed, for example, by expression in microorganisms such as *Escherichia coli* by a known cloning method using a genome DNA derived from *Geobacillus stearothermophilus* as a template and DNA fragments of primers (a) and (b) shown in examples below as PCR primers.

(2-2) Mutagenesis; Introduction of Amino Acid Substitution into i-Site

The method for mutagenesis in an i-site that is responsible for product inhibition only has to follow the method in Patent Document 2, for example. Specifically, mutation to be introduced is not limited provided that it does not cause the loss of the DGC activity of tGs3466 and adequately reduces product inhibition, and example thereof include mutation of 74th residue lysine to alanine and mutation of 77th residue aspartic acid to glutamic acid in the amino acid sequence of tGs3466. In this way, tiGs3466 can be prepared.

(3) Modification of Enzyme (3-1) Amino Acid Mutagenesis

A DGC according to an embodiment of the present invention is characterized by being obtained by mutagenesis of 54th residue asparagine in the amino acid sequence of tiGs3466 to glycine. The method for mutagenesis only has to follow a known method (Nucleic Acids Res. 2004 Aug. 10; 32(14); e115, for example). A DGC with mutation may be sometimes called a mutant DGC.

(3-2) Preparation of Fusion Enzyme

A DGC according to an embodiment of the present invention can be expressed as a fusion enzyme comprised of tiGs3466 into which the mutation above has been introduced and a dimerizable protein. Fusion of an enzyme can be carried out by a known method. For example, a gene coding for a modified tiGs3466 enzyme into which mutation of 54th residue asparagine in the amino acid sequence of tiGs3466 to glycine has been introduced and a gene coding for a dimerizable protein are cloned separately, and therefrom genes are cleaved out with certain restriction enzymes and are then fused together to give a fusion enzyme gene, which is incorporated into a plasmid for expression in *Escherichia coli* or the like. The dimerizable protein may have any mutation provided that it is still dimerizable.

(4) Synthesis of c-di-GMP Using Modified Enzyme

A DGC according to an embodiment of the present invention that is used for synthesizing c-di-GMP can be in the form of a purified enzyme or a crude enzyme solution resulting from expression, in a microorganism such as *Escherichia coli*, of the modified tiGs3466 enzyme into which mutation of 54th residue asparagine in the amino acid sequence of tiGs3466 to glycine has been introduced or an enzyme obtained by fusion of the modified tiGs3466 and a dimerizable protein.

Specifically, treated bacterial cells can be exemplified as the crude enzyme solution and enzymes derived from the treated bacterial cells can be exemplified as the purified enzyme. Bacterial cells can be prepared via culture by a conventional procedure in a medium in which the bacteria can grow, followed by centrifugation or the like to collect the bacterial cells. Bacterial cells of *Escherichia coli*, as a specific example, can be prepared by inoculating a medium such as a broth medium, an LB medium (1% tryptone, 0.5% yeast extract, 1% common salt), and a 2xYT medium (1.6% tryptone, 1% yeast extract, 0.5% common salt) with starter cells, followed by culture at 30 to 50° C. for about 1 to 100 hours with optional stirring and centrifugation of the culture medium so as to collect the bacterial cells.

Examples of the crude enzyme solution include supernatant obtained by centrifugation of bacterial cells disrupted by a common method such as mechanical disruption (with a Waring blender, a French Press, a homogenizer, a mortar, or the like), freeze-thawing, autolysis, drying (by lyophilization, air drying, or the like), enzyme treatment (with lysozyme or the like), sonication, and chemical treatment (with an acid, an alkali, or the like).

Examples of the purified enzyme include a fraction with desired enzyme activity obtained from the treated bacterial cells by an ordinary enzyme purification means (salting-out treatment, isoelectric precipitation treatment, precipitation treatment with an organic solvent, dialysis treatment, various chromatography treatment, or the like).

To the c-di-GMP synthesis system, GTP as a raw material and a DGC according to an embodiment of the present invention as an enzyme are supplied. Preferably, the amount of GTP ranges from 1 to 200 mM and preferably from 10 to 100 mM and the amount of DGC ranges from 0.001 to 50 units/mL, but these ranges are not limitative. To the reaction system, a metal salt such as a magnesium salt and a manganese salt may further be added. Specific examples of the metal salt include magnesium chloride and manganese chloride. The reaction in such a reaction system can be allowed to proceed at not lower than 15° C., preferably at 30 to 50° C., for 0.5 to 100 hours with optional stirring so as to synthesize c-di-GMP.

The raw material GTP causes substrate inhibition in the c-di-GMP synthesis system, and therefore the reaction system can be combined with a GTP supply system comprised of AMP phosphotransferase (PAP) and a polyphosphate-dependent nucleoside 5'-diphosphate kinase (PNDK).

That is, c-di-GMP can be synthesized by allowing the reaction to proceed in the synthesis system that uses not GTP but GMP as a raw material and adopts, as a GTP supply system, addition of polyphosphoric acid ranging, for example, from 1 to 1000 mM and preferably from 30 to 300 mM in terms of inorganic phosphoric acid, PAP ranging, for example, from 0.001 to 50 units/mL, and PNDK ranging, for example, from 0.001 to 50 units/mL thereto, preferably at 30 to 50° C. for 0.5 to 100 hours with optional stirring.

In each reaction above, pyrophosphoric acid resulting from the reaction can cause product inhibition, and therefore an inorganic pyrophosphatase (yPPA) can be added at an amount not lower than 0.001 units/mL and preferably 0.001 to 10 units/mL After the reaction, c-di-GMP produced into the reaction mixture can be isolated and purified by ordinary chromatography treatment with active carbon, an ion exchange resin, or the like.

(5) Other DGCs

A DGC according to an embodiment of the present invention is a DGC having the amino acid sequence shown under SEQ ID NO:10. A DGC with such a composition is higher in DGC activity than tiGs3466G (a DGC having the amino acid sequence shown under SEQ ID NO:6) is. The amino acid sequence shown under SEQ ID NO:10 may be replaced by an amino acid sequence having identity of 90% or higher with the amino acid sequence shown under SEQ ID NO:10, having 352nd residue glycine in the amino acid sequence shown under SEQ ID NO:10 conserved, and with the lack of amino acid sequence KXXD (SEQ ID NO:23) in the i-site. Alternatively, the amino acid sequence shown under SEQ ID NO:10 may be replaced by an amino acid sequence equivalent to the amino acid sequence shown under SEQ ID NO:10 including deletion, substitution, insertion, or addition of one or several amino acids, having 352nd residue glycine in the amino acid sequence shown under SEQ ID NO:10 conserved, and with the lack of amino acid sequence KXXD (SEQ ID NO:23) in the i-site. Alternatively, the amino acid sequence shown under SEQ ID NO:10 may be replaced by an amino acid sequence coded by the base sequence of a nucleic acid that hybridizes, under stringent conditions, with a nucleic acid having a base sequence complementary to a base sequence coding for the amino acid sequence shown under SEQ ID NO:10, having 352nd residue glycine in the amino acid sequence shown under SEQ ID NO:10 conserved, and with the lack of amino acid sequence KXXD (SEQ ID NO:23) in the i-site.

In a DGC according to an embodiment of the present invention, an amino acid therein corresponding to 291st residue asparagine in a DGC derived from *Geobacillus stearothermophilus* may be substituted by a glycine residue. Such an amino acid corresponding to 291st residue asparagine may be located, for example, by comparing the sequence of the DGC in question with the sequence of the DGC derived from *Geobacillus stearothermophilus* and then select an amino acid residue corresponding to 291st residue asparagine of the DGC derived from *Geobacillus stearothermophilus*. The DGC derived from *Geobacillus stearothermophilus* may be a DGC having the amino acid sequence shown under SEQ ID NO:25, for example.

A DGC according to an embodiment of the present invention may be a fusion enzyme resulting from fusion of a DGC and a protein or a peptide. The protein for fusion is preferably a dimerizable protein. The protein for fusion may be an enzyme that hydrolyzes pyrophosphoric acid. It is verified in examples below, for example, that a DGC to which a dimerizable inorganic pyrophosphatase is fused is remarkably improved in efficiency of c-di-GMP production. A DGC according to an embodiment of the present invention may be a protein fragment provided that it maintains DGC activity.

The DGC activity of a DGC according to an embodiment of the present invention is significantly higher than that of a conventional DGC or tiGs3466, by a factor of 1.2, 1.5, 1.8, 2.0, 3.0, 5.0, or 10.0, even higher, or between any two of these. The term "significantly" includes, for example, the case where Student's t-test (one-sided test or two-sided test) gives a statistically significant difference and p<0.05 is satisfied.

After heat treatment under conditions of pH7.8 and 50° C. for 60 minutes, the remaining activity of a DGC according to an embodiment of the present invention may be, for example, 80, 90, or 100%, even higher, or between any two of these. The same applies to the case where heat treatment lasts for 10 or 30 minutes. The remaining activity of a DGC according to an embodiment of the present invention after heat treatment is significantly higher than that of a conventional DGC or tiGs3466. The DGC activity may be, for example, 1.5, 2.0, 5.0, 10.0, 20.0, or 30.0 times higher, even higher, or between any two of these.

The molecular weight of a DGC according to an embodiment of the present invention may be 19800±2000, specifically 17800, 18300, 18800, 19300, 19800, 20300, 20800, 21300, or 21800, for example, or between any two of these. The molecular weight of a DGC according to an embodiment of the present invention may be about 19800. The molecular weight may be a value (Da) measured by SDS-polyacrylamide gel electrophoresis.

The optimum pH may be 7.3, 7.70, 7.85, 8.0, 8.5, 9.05, 9.15, or 9.4 or between any two of these. The optimum pH may be about 8.0 to about 8.5. The optimum pH may be a pH at which, with the activity at pH8.0 being 100, the relative activity is 60, 70, 80, or 90% thereof or higher. With the activity of a DGC according to an embodiment of the present invention at pH8.0 being 100, the relative activity at pH9.5 may be not higher than 55% thereof.

The optimum temperature may be 35, 40, 45, 50, 55, or 60° C. or between any two of these. The optimum temperature may be about 55° C. The optimum temperature may be a temperature at which, with the activity at 55° C. being 100, the relative activity is 60, 70, 80, or 90% thereof or higher.

An embodiment of the present invention is a c-di-GMP material containing a DGC according to an embodiment of the present invention. The c-di-GMP material may contain an aqueous solution or a sol, for example, at a pH within the range of the optimum pH of a DGC according to an embodiment of the present invention. The c-di-GMP material can be combined with an inorganic pyrophosphatase for use as a kit for c-di-GMP production.

An embodiment of the present invention is a polynucleotide coding for a DGC according to an embodiment of the present invention. An embodiment of the present invention is a vector harboring the polynucleotide. An embodiment of the present invention is a transformant resulting from transformation with the polynucleotide or the vector. By using the polynucleotide, the vector, or the transformant, a DGC according to an embodiment of the present invention can be produced. The transformant includes a cell or a living organism.

An embodiment of the present invention is a method for producing c-di-GMP with the use of a GTP supply system comprised of PAP and PNDK. In this production method, a DGC according to an embodiment of the present invention, GMP, polyphosphoric acid, PAP, and PNDK are used. This production method can prevent a decrease in production efficiency caused by substrate inhibition. To the reaction solution, yPPA, magnesium chloride, and/or manganese chloride may be added.

In the present specification, the term "amino acid" collectively refers to organic compounds having an amino group and a carboxy group and includes, but is not particularly limited to, Ala, Arg, Asn, Asp, Cys, Gln, Glu, Gly, His, Ile, Leu, Lys, Met, Phe, Pro, Ser, Thr, Trp, Tyr, and Val, for example. When a DGC according to an embodiment of the present invention has a specific amino acid sequence, any amino acid in the amino acid sequence may be chemically modified, and in such a case, the DGC according to an embodiment of the present invention is still regarded as having that specific amino acid sequence. As chemical modification that an amino acid of a protein generally receives in a living organism, N-terminus modification (acetylation and myristoylation, for example), C-terminus modification (amidation and addition of glycosylphosphatidylinositol, for example), and side chain modification (phosphorylation and glycosylation, for example) are known, for example.

In the present specification, the term "polynucleotide" encompasses a plurality of nucleotides, bases, or equivalents thereof that are bonded to each other. The nucleotides and the bases include DNA bases and RNA bases. The equivalents include, for example, DNA bases and RNA bases that have chemical modification such as methylation, and nucleotide analogs. The nucleotide analogs include non-natural nucleotides. The term "DNA strand" refers to two or more DNA bases or equivalents thereof being linked to each other. The term "RNA strand" refers to two or more RNA bases or equivalents thereof being linked to each other. The term "base sequence" refers to a sequence of a nucleotide or an equivalent thereof constituting a polynucleotide. The base sequence is generally expressed with A (adenine), G (guanine), C (cytosine), and T (thymine) T can be read as U (uracil) according to the situation, and vice versa. When a polynucleotide has a specific base sequence comprised of A, G, C, T, or U, any base in the base sequence may be replaced by its equivalent, and in such a case, the polynucleotide is still regarded as having that specific base sequence. The polynucleotide can be synthesized by a DNA/RNA synthesizer or be purchased from a contractor (Invitrogen Limited, Takara Bio Inc., for example) engaged in the contract synthesis of DNA bases and/or RNA bases.

As the "vector" in the present specification, an *Escherichia coli* plasmid (pBR322, pUC12, pET-Blue-2, for example), a *Bacillus subtilis* plasmid (pUB110, pTP5, for example), a yeast plasmid (pSH19, pSH15, for example), an animal cell expression plasmid (pA1-11, pcDNAI/Neo, for example), a bacteriophage such as a λ phage, a vector derived from a virus such as adenoviruses, retroviruses, and baculoviruses, or the like can be used. Such a vector may harbor a component essential for protein expression, such as a promoter, a replication origin, and an antibacterial resistance gene. The vector may be an expression vector.

In the present specification, when a DGC includes deletion, substitution, insertion, or addition of one or several amino acids, the term "several" may indicate 15, 10, 8, 6, 4, or 2 or a number smaller than any of these. The number is preferably as small as possible because the smaller the number indicated by the term "several" is, the closer the properties of the DGC are to those of a DGC that includes no deletion nor the like in its amino acid sequence. It is generally known that a polypeptide in which one or several amino acid residues are deleted, added, inserted, or substituted with another amino acid or other amino acids maintains the biological activity (Mark et al., Proc Natl Acad Sci USA. 1984 September; 81(18):5662-5666, Zoller et al., Nucleic Acids Res. 1982 Oct. 25; 10(20):6487-6500, Wang et al., Science. 1984 Jun. 29; 224(4656):1431-1433).

In the present specification, when one or several amino acids in a DGC are substituted with other amino acids, the substitution preferably conserves the characteristics of the amino acid side chain Examples of amino acids with side chains sharing characteristics include hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy-containing side chain (S, T, Y), amino acids having a sulfur-containing side chain (C, M), amino acids having a carboxylic acid- and amide-containing side chain (D, N, E, Q), amino acids having a base-containing side chain (R, K, H), and amino acids having an aromatic-containing side chain (H, F, Y, W) (each letter in parentheses is a one-letter code of an amino acid). Substitution between amino acids within each group is collectively called "conservative substitution".

In the present specification, "90% or higher" as identity between the amino acid sequences of DGCs may be 90, 95, 98, 99, or 100%, for example, higher than any of these, or between any two of these. The numerical value is preferably as large as possible because the larger the numerical value that "90% or higher" refers to is, the closer the properties of one of the DGCs are to those of the other DGC.

In the present specification, the term "identity" generally refers to the proportion of the same amino acid alignments between two or among a plurality of amino acid sequences determined by calculation by a method known in the technical field. Prior to determining the proportion by calculation, the amino acid sequences to be compared are properly aligned and, when necessary to maximize the proportion of identity, space is inserted into the amino acid sequences. The method for proper alignment, the method for determining the proportion by calculation, the method for comparison, and related computer programs are conventionally well known in the technical field (BLAST and GENETYX, for example). In the present specification, "homology" can be expressed by numerical values determined by BLAST in NCBI (http://www.ncbi.nlm.nih.gov/) unless otherwise indicated. In comparison between or among amino acid sequences by BLAST, Blastp can be used as the Algorithm by default, and the results are converted into numerical values as Positives or Identities. Alternatively, "identity" is the proportion of the same base alignments determined by calculation between two or among a plurality of base sequences in the same manner as above by a method known in the technical field. Blastn can be used as the Algorithm in BLAST by default.

In the present specification, "stringent conditions" can be, for example, the following conditions: (1) washing at low ionic strength at a high temperature (at 50° C. in 0.015-M sodium chloride/0.0015-M sodium citrate/0.1% sodium dodecyl sulfate, for example), (2) using a denaturant such as formamide in hybridization (at 42° C. in 50% (v/v) formamide, 0.1% bovine serum albumin/0.1% Ficoll/0.1% polyvinylpyrrolidone/50-mM sodium phosphate buffer at pH6.5, 750-mM sodium chloride, and 75-mM sodium citrate, for example), or (3) overnight incubation in a solution containing 20% formamide, 5×SSC, 50-mM sodium phosphate (pH7.6), 5×Denhardt's solution, 10% dextran sulfate, and 20-mg/ml modified, sheared salmon sperm DNA at 37° C., followed by washing the filter at about 37 to 50° C. with 1×SSC. The concentration of formamide may be 50% or higher. Duration of washing may be 5, 15, 30, 60, or 120 minutes, or longer. Stringency of the hybridization reaction is possibly affected by a plurality of factors such as a temperature and a salt concentration, and for the details thereof, Ausubel et al., Current Protocols in Molecular Biology, Wiley Interscience Publishers (1995) can be referred to.

The embodiments of the present invention are described above. These are examples of the present invention, and various other configurations can be adopted. The configurations described in the embodiments can be adopted in combination.

EXAMPLES

The present invention will be described more specifically by examples. Obviously, the present invention is not limited to these examples. In examples, the methods for DNA preparation, cleavage with restriction enzymes, DNA linkage with T4 DNA ligase, and transformation of *Escherichia coli* followed "Molecular Cloning, A Laboratory Manual, Second Edition" (Cold Spring Harbor Laboratory, Cold Spring Harbor, N.Y. (1989)). The amount of nucleotide in a reaction mixture was determined by HPLC. FIG. 1 is a conceptual view of the procedure for preparing various plasmids in examples.

Example 1

Introduction of Site-Specific Mutation into tiGs3466

(1) Identification and Cloning of c-di-GMP Synthase Gene

The DGC gene of *Geobacillus stearothermophilus* was not yet identified and was therefore first searched for by using the genome DNA sequence information of *Geobacillus kaustophilus* (Accession No BA000043) that had its genome DNA sequence known. The genome DNA sequence of *Geobacillus kaustophilus* was searched by tBLASTn program for a DNA region coding for an open reading frame (hereinafter, abbreviated as ORF) that was similar to the amino acid sequence of GGDEF (SEQ ID NO:26) domain in PleD derived from *Caulobacter crescentus* having activity to synthesize c-di-GMP. The results gave an unidentified DNA sequence expected to be DGC gene. The information of the unidentified DNA sequence was used in an attempt to clone a gene homolog thereof (hereinafter, sometimes called "Gs3466 gene") in *Geobacillus stearothermophilus* strain TH6-2. The strain TH6-2 was internationally deposited as FERM BP-10466 on Dec. 7, 2005 with the International Patent Organism Depositary at National Institute of Advanced Industrial Science and Technology.

Using the chromosome DNA derived from *Geobacillus stearothermophilus* strain TH6-2 as a template and (a) and (b) as primers, PCR was performed to amplify a gene coding for a DGC including deletion of an amino acid residue at the N-terminal region:

(a)
(SEQ ID NO: 11)
AACCATGGGACTCCGAGCACGACCGATTAT (b)
(SEQ ID NO: 12)
AAACTCGAGCCCGCATTGGGCTGATAC.

The resultant DNA fragment was cleaved with restriction enzymes NcoI and XhoI, while plasmid pET-Blue-2 (obtained from Novagen) was also digested with restriction enzymes NcoI and XhoI. Then, the resultant two DNA fragments were linked with T4 DNA ligase, followed by transformation of *Escherichia coli* strain JM109. From the resultant ampicillin-resistant transformant, plasmid pET-tGs3466 was isolated.

Plasmid pET-tGs3466 was a plasmid harboring a DNA fragment containing a gene (hereinafter, sometimes called tGs3466 gene) coding for the 239th to 408th amino acid residues of Gs3466. Analysis of the base sequence of the gene thus cloned revealed that tGs3466 gene had the DNA base sequence shown under SEQ ID NO:1. Translation of the DNA base sequence into an amino acid sequence revealed that tGs3466 had the amino acid sequence shown under SEQ ID NO:2. The amino acid sequence of tGs3466 had 34% homology with the amino acid sequence of GGDEF (SEQ ID NO:26) domain of a DGC (PleD) derived from *Caulobacter crescentus*.

A DGC has a site called an i-site that is a c-di-GMP-binding site and is responsible for causing product inhibition. In order to avoid product inhibition, site-specific mutation was introduced into the i-site of pET-tGs3466. Introduction of site-specific mutation was carried out according to a known method (Nucleic Acids Res. 2004 Aug. 10; 32(14):e115) using the following primers (c) and (d) in mutagenesis:

(c)
(SEQ ID NO: 13)
GTTTCTCGCAGAGGGCGAATTCTTGTTCCGCAGCGG (d)
(SEQ ID NO: 14)
CGCCCTCTGCGAGAAACTGTTTCAAGGTTGAG.

As a result, plasmid pET-tiGs3466 was isolated. Plasmid pET-tiGs3466 was a plasmid harboring a DNA fragment that was the 239th to 408th amino acid residues of Gs3466 and contained a gene (hereinafter, sometimes called "tiGs3466 gene") coding for a protein including mutation at the 311th and 314th amino acid residues of Gs3466 corresponding to the i-site. Analysis of the base sequence of the gene thus cloned revealed that tiGs3466 gene had the DNA base sequence shown under SEQ ID NO:3. Translation of the DNA base sequence into an amino acid sequence revealed that tiGs3466 had the amino acid sequence shown under SEQ ID NO:4. The full-length DNA base sequence of Gs3466 gene was found to be the base sequence shown under SEQ ID NO:24, and translation thereof into an amino acid sequence revealed that Gs3466 had the amino acid sequence shown under SEQ ID NO:25.

(2) Introduction of Site-Specific Mutation into tiGs3466

PCR was performed with the following primers (q) and (r) to introduce mutation into 54th residue asparagine of tiGs3466:

(q)
(SEQ ID NO: 15)
CACGTATGGCCATGCCGTCGGCGACGA (r)
(SEQ ID NO: 16)
CGGCATGGCCATACGTGTCGTTGATCGTTTTAAA.

The DNA resulting from the amplification reaction was purified and was then treated with restriction enzyme DpnI. The resultant DNA was used to transform *Escherichia coli* strain JM109, and from the resultant ampicillin-resistant transformant, plasmid pET-tiGs3466G was isolated.

Plasmid pET-tiGs3466G was a plasmid harboring a DNA fragment that contained a gene (hereinafter, sometimes called "tiGs3466G gene") coding for a protein that included mutation of 54th residue asparagine in the amino acid sequence of tiGs3466 to glycine. Analysis of the base sequences of the both genes thus cloned revealed that tiGs3466G gene had the DNA base sequence shown under SEQ ID NO:5. Translation of the DNA base sequence into an amino acid sequence revealed that tiGs3466G had the amino acid sequence shown under SEQ ID NO:6. Plasmid pET-tiGs3466G was used to transform *Escherichia coli* Tuner (DE3) pLacI, and a transformant was obtained.

Subsequently, the DGC activity (unit) of a crude enzyme solution was measured and calculated by a method shown below. To a 50-mM Tris-hydrochloride buffer (pH8.0) containing 10-mM magnesium chloride, 1-mM manganese chloride, and 2-mM GTP, 0.6 mg/mL of a purified enzyme solution resulting from purification of the transformant was added, and the temperature was maintained at 37° C. so as to carry out a reaction, which was then stopped by heat treatment at 100° C. for 30 seconds. The amount of nucleotide in the reaction mixture was determined by HPLC, and the activity of the enzyme to produce 1 mole of pppGpG and c-di-GMP at 37° C. in 1 minute was defined as 1 unit. Here, the purified enzyme was obtained by purification by the same method as in Example 2 (3) below.

The results of measuring DGC activity using tiGs3466 and tiGs3466G are shown in Table 1.

TABLE 1

|  | specific activity (units/mg) |
|---|---|
| tiGs3466 | 0.017 |
| tiGs3466G | 0.056 | tiGs3466G, which was a single amino acid mutant of tiGs3466, was proved to have specific activity 3.3 times as high as unmodified tiGs3466.

The thermal stability of both of the enzymes was also evaluated. Each enzyme was subjected to heat treatment at pH7.8 at 50° C. and was sampled 0, 10, 30, and 60 minutes into the treatment for measuring the activity. With the activity at 0 minute into the heat treatment being defined as 100(%), the remaining activity is shown in Table 2.

TABLE 2

|  | Remaining activity (%) | | | |
|---|---|---|---|---|
|  | 0 min | 10 min | 30 min | 60 min |
| tiGs3466 | 100.0 | 37.5 | 11.9 | 3.3 |
| tiGs3466G | 100.0 | 101.0 | 107.1 | 102.3 |

The results proved that, compared to unmodified tiGs3466 that rapidly lost its activity due to heat treatment, tiGs3466G had high thermal stability, which was very preferable for a c-di-GMP synthase.

Example 2

Development of Fusion tiGs3466

(1) Cloning of Fusion tiGs3466

Cloning of a fusion product of tiGs3466 and a dimer-forming protein (dimerizable protein) started with cloning of tiGs3466. For cloning, PCR was performed using primers (e) and (f) below and plasmid pET-tiGs3466 in Example 1 as a template:

(e)
(SEQ ID NO: 17)
AAGAGCTCGGTGGCGGTGGCTCGGGCGGTGGTGGGTCGGACCACTTCGA

AAAAATGGC (f)
(SEQ ID NO: 18)
AAACTCGAGCCCGCATTGGGCTGATAC.

The DNA fragment resulting from PCR amplification was cleaved with restriction enzymes SacI and XhoI, and the resultant was subjected to cloning into the SacI-XhoI site of pET-Blue-2, whereby plasmid pET-linker-tiGs3466 was isolated. Plasmid pET-linker-tiGs3466 was pET-Blue-2 in which, into the SacI-XhoI-cleaved site downstream from pET promoter, tiGs3466 gene having a DNA sequence coding for 10 amino acid residues GGGGSGGGGS (SEQ ID N0:28) added to its N-terminus was inserted.

Then, as a dimerizable protein, an inorganic pyrophosphatase (yPPA) derived from *Saccharomyces cerevisiae* was used. Expression of tiGsDGC to which yPPA had been fused started with PCR amplification of yPPA gene using the genome DNA of *Saccharomyces cerevisiae* as a template and primers (g) to (j). Subsequently, following treatment with restriction enzyme NcoI-SacI, cloning was performed into the NcoI-SacI site of plasmid pET-linker-tiGs3466.

(g)

CATGCCATGGCCTACACTACCAGACAAA (SEQ ID NO: 19)

(h)

GTTAGAAACTGTTTCCCTCATCATGGTTACATTCACAACT (SEQ ID NO: 20)

(i)

AACCATGATGAGGGAAACAGTTTCTAAC (SEQ ID NO: 21)

(j)

TTGAGCTCAACAGAACCGGAGATGAAGAACC (SEQ ID NO: 22)

PCR followed a conventional procedure except that, in amplification of yPPA gene, silent mutation was introduced by SOE-PCR technique (Gene. 1989 Apr. 15; 77(1):51-9) so as to remove the NcoI-cleaved site in the sequence. Specifically, a 603-bp DNA fragment obtained by PCR using primers (g) and (h) and a 261-bp DNA fragment obtained by PCR using primers (i) and (j) were used as templates to carry out PCR using primers (g) and (j), whereby a desired 864-bp DNA fragment was obtained.

As a result of cloning, plasmid pET-yPPAtiGs3466 was obtained from the transformed bacterial cell. Plasmid pET-yPPAtiGs3466 was a plasmid harboring the DNA sequence of a gene (hereinafter, sometimes called "yPPA-tiGs3466 gene") coding for a fusion enzyme that resulted from fusion of yPPA to the N-terminus of tiGs3466 with a linker sequence interposed therebetween. An NcoI-XhoI DNA fragment having yPPA-tiGs3466 gene was inserted into pET-Blue-2 at the NcoI-XhoI-cleaved site downstream from pET promoter. Analysis of the base sequence of the fusion enzyme gene thus cloned revealed that yPPA-tiGs3466 gene had the DNA base sequence shown under SEQ ID NO:7. Translation of the DNA base sequence into an amino acid sequence revealed that yPPA-tiGs3466 had the amino acid sequence shown under SEQ ID NO:8.

(2) Preparation of DGC Enzyme Solution

*Escherichia coli* strain Tuner (DE3) pLacI was transformed with the plasmid harboring tiGs3466 gene and yPPA-tiGs3466 gene. The resultant strain was inoculated in 50 mL of a 2xYT medium containing 100 μg/mL of ampicillin and 0.15% glucose, followed by shake culture at 37° C. When 4×10⁸ cells/mL was reached, the culture medium was cooled to 30° C. and IPTG was added to achieve the final concentration of 1 mM, followed by shake culture continued overnight. After the completion of culture, bacterial cells were collected by centrifugation (10,000×g, 10 minutes), followed by suspension in 5 mL of a buffer (containing 50-mM Tris-hydrochloride (pH7.8), 500-mM NaCl, and 20-mM imidazole) and then sonication to disrupt the bacterial cells. Another round of centrifugation (10,000× g, 10 minutes) was performed to remove the residue of bacterial cells. The resultant supernatant fraction was purified with an Ni-sepharose resin. The protein concentration in the purified enzyme was measured with a protein assay kit (Bio-Rad Laboratories, Inc.).

(3) Measurement of Activity of Enzyme tiGs3466 and Fusion Enzyme

The DGC activity (unit) of the crude enzyme solution was measured and calculated by the following method. To a 50-mM Tris-hydrochloride buffer (pH8.0) containing 10-mM magnesium chloride, 1-mM manganese chloride, and 2 mM-GTP, 0.6 mg/mL of the purified enzyme solution was added, and the temperature was maintained at 37° C. so as to carry out a reaction, which was then stopped by heat treatment at 100° C. for 30 seconds. The amount of nucleotide in the reaction mixture was determined by HPLC, and the activity of the enzyme to produce 1 mole of pppGpG and c-di-GMP at 37° C. in 1 minute was defined as 1 unit.

DGC relative activity when tiGs3466, the fusion enzyme (yPPA-tiGs3466), or yPPA at a weight (about 0.36 mg/mL) equivalent to the weight of yPPA in the fusion enzyme (tiGs3466+yPPA) was added to the reaction mixture is shown in Table 3.

TABLE 3

| Enzyme | Relative activity (%) |
|---|---|
| tiGs3466 | 100 |
| yPPA-tiGs3466 | 262 |
| tiGs3466 + yPPA | 97 |

Table 3 revealed that, although no enhancement in activity was observed when yPPA was added to tiGs3466, the DGC activity of the fusion enzyme with yPPA was enhanced compared to untreated tiGs3466. It was assumed that, in the fusion enzyme, dimer formation between yPPAs facilitated dimerization of tiGs3466 with another tiGs3466.

Example 3

Preparation of yPPA-tiGs3466G

In order to combine two enzyme modifications in Example 1 and Example 2 so as to prepare a fusion enzyme comprised of yPPA and tiGs3466G, cloning was performed as follows.

PCR was performed using two primers (e) and (f) and plasmid pET-tiGs3466G prepared in the earlier section as a template, followed by treatment with restriction enzymes SacI and XhoI and then cloning into the SacI-XhoI site of plasmid pET-yPPAtiGs3466. From the resultant transformant, plasmid pET-yPPAtiGs3466G was isolated. Plasmid pET-yPPAtiGs3466G was a plasmid harboring a DNA fragment containing a gene (hereinafter, sometimes called "yPPA-tiGs3466G gene") coding for a fusion enzyme that resulted from binding of yPPA to the N-terminus of tiGs3466G with a linker sequence interposed therebetween. Analysis of the base sequences of both of the genes thus cloned revealed that yPPA-tiGs3466G gene had the DNA base sequence shown under SEQ ID NO:9. Translation of the DNA base sequence into an amino acid sequence revealed that yPPA-tiGs3466G had the amino acid sequence shown under SEQ ID NO:10. *Escherichia coli* Tuner (DE3) pLacI was transformed with plasmid pET-yPPAtiGs3466G to give a transformant, and the method in Example 2 (3) was followed to prepare a purified enzyme.

After the concentration of the purified enzyme was adjusted to 0.1 mg/mL, the activity of the purified enzyme was measured by the activity measurement system in Example 1. As a result, as shown in Table 4, tiGs3466G and mutant yPPA-tiGs3466G were remarkably enhanced in specific activity compared to unmodified enzyme tiGs3466. The amino acid sequence of each enzyme is shown in Table 5.

TABLE 4

| Enzyme | Specific activity (units/mg) |
|---|---|
| tiGs3466 | 0.017 |
| yPPA-tiGs3466 | 0.046 |

TABLE 4-continued

| Enzyme | Specific activity (units/mg) |
|---|---|
| tiGs3466G | 0.056 |
| yPPA-tiGs3466G | 0.137 |

TABLE 5

```
tGs3466 (SEQ ID NO: 2)
MDHFEKMAYTDFLTGIHNRAYMDQTIAKLNGSGEWIGVVVADIDNFKTINDTYNHAVGDEVI
RHFASTLKQFLKEGDFLFRSGGEEFTMFLRNRTFEESVRLVEEIREAVRHSTVLVDYMAAKR
PIAYTSSFGLYFCQAEGTMSIEKAYIYADHLLLRSKESGKNKVSAQCGLE tiGs3466 (SEQ ID NO: 4)
MDHFEKMAYTDFLTGIHNRAYMDQTIAKLNGSGEWIGVVVADIDNFKTINDTYNHAVGDFVI
RHFASTLKQFLAEGEFLFRSGGEEFTMFLRNRTFEESVRLVEEIREAVRHSTVLVDYMAAKR
PIAYTSSFGLYFCQAEGTMSIEKAYIYADHLLLRSKESGKNKVSAQCGLE tiGs3466G (SEQ ID NO: 6)
MDHFEKMAYTDFLTGIHNRAYMDQTIAKLNGSGEWIGVVVADIDNFKTINDTYGHAVGDEVI
RHFASTLKQFLAEGEFLFRSGGEEFTMFLRNRTFEESVRLVEEIREAVRHSTVLVDYMAAKR
PIAYTSSFGLYFCQAEGTMSIEKAYIYADHLLLRSKESGKNKVSAQCGLE yPPA-tiGs3466 (SEQ ID NO: 8)
MAYTTRQIGAKNTLEYKVYIEKDGKPVSAFHDIPLYADKENNIFNMVVEIPRWTNAKLEITKE
ETLNPIIQDTKKGKLRFVRNCFPHHGYIHNYGAFPQTWEDPNVSHPETKAVGDNDPIDVLEI
GETIAYTGQVKQVKALGIMALLDEGETDWKVIAIDINDPLAPKLNDIEDVEKYFPGLLRATNE
WFRIYKIPDGKPENQFAFSGEAKNKKYALDIIKETHDSWKQLIAGKSSDSKGIDLTNVTLPDT
PTYSKAASDAIPPASPKADAPIDKSIDKWFFISGSVELGGGGSGGGGSDHFEKMAYTDFLTGI
HNRAYMDQTIAKLNGSGEWIGVVVADIDNFKTINDTYNHAVGDEVIRHFASTLKQFLAEGEF
LFRSGGEEFTMFLRNRTFEESVRLVEEIREAVRHSTVLVDYMAAKRPIAYTSSFGLYFCQAEG
TMSIEKAYIYADHLLLRSKESGKNKVSAQCGLE yPPA-tiGs3466G (SEQ ID NO: 10)
MAYTTRQIGAKNTLEYKVYIEKDGKPVSAFHDIPLYADKENNIFNMVVEIPRWTNAKLEITKE
ETLNPIIQDTKKGKLRFVRNCFPHHGYIHNYGAFPQTWEDPNVSHPETKAVGDNDPIDVLEI
GETIAYTGQVKQVKALGIMALLDEGETDWKVIAIDINDPLAPKLNDIEDVEKYFPGLLRATNE
WFRIYKIPDGKPENQFAFSGEAKNKKYALDIIKETHDSWKQLIAGKSSDSKGIDLTNVTLPDT
PTYSKAASDAIPPASPKADAPIDKSIDKWFFISGSVELGGGGSGGGGSDHFEKMAYTDFLTGI
HNRAYMDQTIAKLNGSGEWIGVVVADIDNFKTINDTYGHAVGDEVIRHFASTLKQFLAEGEF
LFRSGGEEFTMFLRNRTFEESVRLVEEIREAVRHSTVLVDYMAAKRPIAYTSSFGLYFCQAEG
TMSIEKAYIYADHLLLRSKESGKNKVSAQCGLE
```

Example 4

Reaction for c-di-GMP Synthesis Using Purified Enzyme DGC (1) Preparation of Polyphosphate:AMP Phosphotransferase (PAP) Derived from *Acinetobacter johnsonii*

PAP was prepared from *Acinetobacter johnsonii* by a method described in a known literature (WO03/100056), and the activity was measured. The amount of ATP in the reaction mixture was determined by high-performance liquid chromatography (HPLC), and the activity of the enzyme to produce 1 mole of ADP in 1 minute was defined as 1 unit.

(2) Preparation of Polyphosphate-Dependent Nucleoside 5'-Diphosphate Kinase (PNDK) from *Pseudomonas aeruginosa*

PNDK was prepared from *Pseudomonas aeruginosa* strain PAO1 by a method described in a known literature (WO2006/080313), and the activity was measured. The amount of ATP in the reaction mixture was determined by high-performance liquid chromatography (HPLC), and the activity of the enzyme to produce 1 mole of ATP at 37° C. in 1 minute was defined as 1 unit.

(3) Preparation of Inorganic Pyrophosphatase (yPPA)

yPPA was obtained from Roche Diagnostics. The activity was measured by a method described in a known literature (WO2006/080313), where the amount of the product was determined and the activity of inorganic pyrophosphatase to produce 2 μmol of inorganic phosphoric acid in 1 minute was defined as 1 unit.

Figure 2:
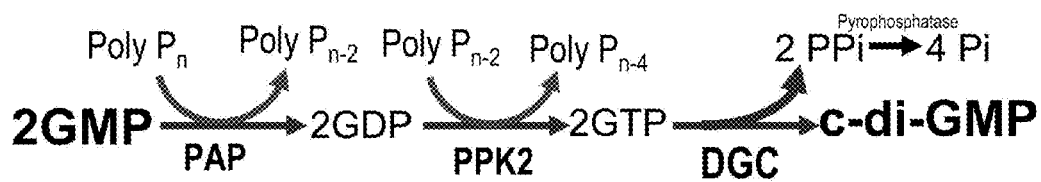
FIG. 2 is a schematic view of reaction steps in a c-di-GMP synthesis system in which a GTP supply system is used.

(4) Synthesis of c-di-GMP Combined with GTP Supply System Comprised of PAP and PNDK Synthesis of c-di-GMP was performed with the use of a GTP supply system. FIG. 2 is a schematic view of the reaction steps in this synthesis system. Specific reaction procedure was as follows.

Figure 3:
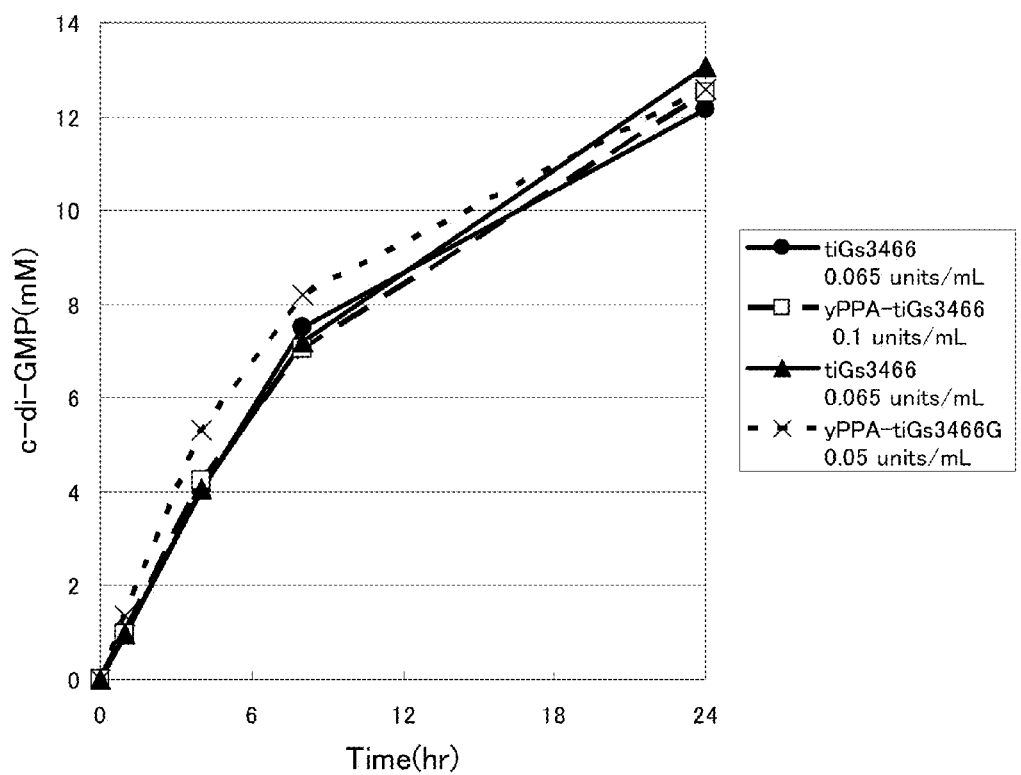
FIG. 3 shows how c-di-GMP synthesis proceeds when modified enzymes used in examples are in a purified state. The abscissa indicates reaction time, and the ordinate indicates the concentration of c-di-GMP in a culture medium.

To 200 mL of a 50-mM aqueous Tris-hydrochloride buffer (pH9.0) containing 20-mM magnesium chloride, 40-mM GMP, 1-mM manganese chloride, and polyphosphoric acid (50 mM in terms of inorganic phosphoric acid), PAP (0.5 units/mL), PNDK (1.0 units/mL), and a DGC at each unit value shown in Table 6 were added, and then reaction was initiated at 37° C. At 8 hours into the reaction, polyphosphoric acid was added at an amount equivalent to 50 mM of inorganic phosphoric acid, and the reaction was continuously allowed to proceed. When tiGs3466 and tiGs3466G were used in the synthesis reaction, an inorganic pyrophosphatase (1.0 units/mL) was further added. The results showed that the amount of c-di-GMP production at 24 hours into the reaction reached about 12.6 mM (63% in terms of ½ GMP conversion) regardless of the enzyme used (FIG. 3). The amount in Table 6 was determined based on the unit value determined in the activity measurement above.

As described above, each of the modified enzymes of the present invention revealed to have adequate DGC activity.

TABLE 6

| Enzyme | Amount |
|---|---|
| tiGs3466 | 0.065 units/mL |
| yPPA-tiGs3466 | 0.10 units/mL |
| tiGs3466G | 0.065 units/mL |
| yPPA-tiGs3466G | 0.050 units/mL |

Based on the amount of purified enzyme collected per unit amount of culture medium, the amount of bacterial cells required to be cultured for synthesizing the same amount of c-di-GMP relative to the total amount of the reaction mixture was calculated, and the results are shown in Table 7.

TABLE 7

|  | Amount of enzyme required (units/mL-RM) | Amount of purified enzyme collected (units/mL-culture) | Amount of culture required (with amount of reaction mixture being 1) |
|---|---|---|---|
| tiGs3466 | 0.065 | 0.0047 | 13.9 |
| yPPA-tiGs3466 | 0.10 | 0.016 | 6.2 |
| tiGs3466G | 0.065 | 0.019 | 3.4 |
| yPPA-tiGs3466G | 0.050 | 0.022 | 2.2 |

The results revealed that the modified enzyme of the present invention was able to remarkably reduce the amount of culture required for enzyme preparation.

Example 5

Reaction for c-di-GMP Synthesis Using Crude Enzyme DGC (1) Measurement of Specific Activity of Enzyme In order to omit the enzyme purification step, c-di-GMP synthesis using a crude enzyme as enzyme DGC was studied.

Bacterial cells for enzyme production cultured in the same method as above were suspended in 5 mL of a 50-mM Tris-hydrochloride buffer (pH7.8), and the resultant was subjected to sonication to disrupt the bacterial cells, followed by centrifugation to give supernatant. The supernatant was to be used as a crude enzyme solution, and the DGC enzyme activity was measured. Activity measurement was performed in the same manner as in the measurement system for purified enzyme in Example 1, with each crude enzyme solution at an amount in the following table added to the reaction system to allow the reaction to proceed.

Activity per unit amount of crude enzyme solution and activity per unit amount of protein (specific activity) were calculated and are shown in Table 8.

TABLE 8

|  | Amount of crude enzyme solution | Activity of crude enzyme solution (units/ml) | Specific activity of crude enzyme solution (units/mg) |
|---|---|---|---|
| tiGs3466 | 10% | 0.018 | 0.001 |
| yPPA-tiGs3466 | 5% | 0.190 | 0.012 |
| tiGs3466G | 10% | 0.223 | 0.015 |
| yPPA-tiGs3466G | 5% | 0.262 | 0.043 |

Comparison of the activity of crude enzyme solutions of the crude enzymes showed that the modified enzyme of the present invention was significantly enhanced in specific activity compared to unmodified tiGs3466.

(2) Synthesis of c-di-GMP Using Crude Enzyme

Synthesis reaction using a crude enzyme was studied. Synthesis reaction was carried out under the same conditions as in Example 4 (4), with 1.0 unit/mL of yPPA added to the reaction of tiGs3466 or tiGs3466G. The amount of each enzyme to be added was determined as follows depending on the activity of the crude enzyme:

| yPPA-tiGs3466 | 0.075 units/mL |
| tiGs3466G | 0.075 units/mL |
| yPPA-tiGs3466G | 0.075 units/mL |
| tiGs3466 | equivalent to 0.065 units/mL |

(the amount of tiGs3466 calculated from the activity of the crude enzyme was too large to be practical and therefore, based on the amount thereof in the crude enzyme solution estimated from the amount of enzyme collected at the time of enzyme purification, the crude enzyme was added at an amount 1.4 times the amount of the reaction mixture).

Figure 4:
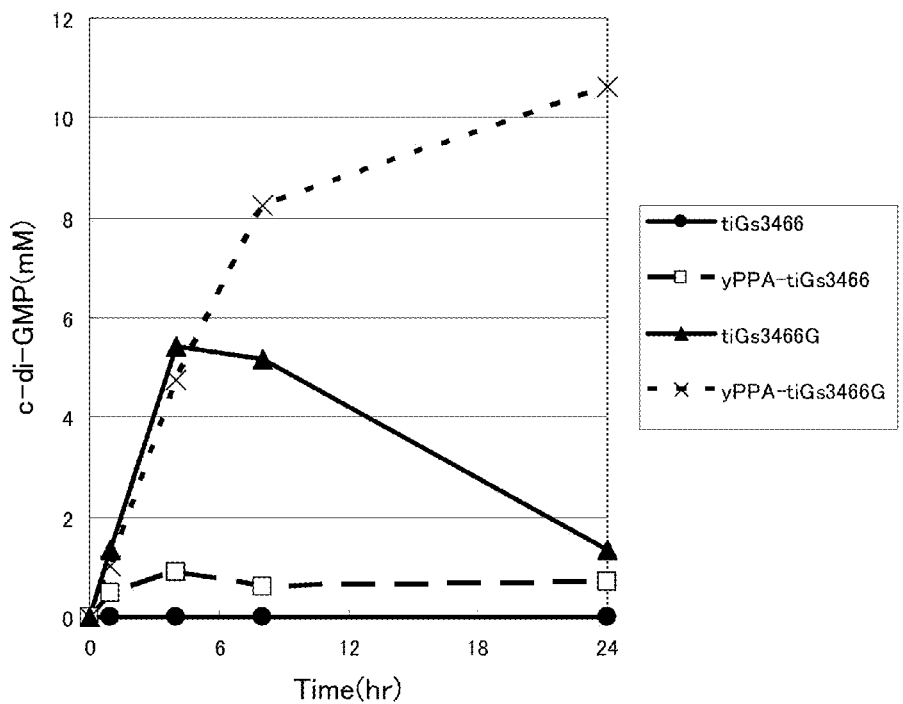
FIG. 4 shows how c-di-GMP synthesis proceeds when modified enzymes used in examples are in a crude state. The abscissa indicates reaction time, and the ordinate indicates the concentration of c-di-GMP in a culture medium.

The results proved that, as shown in FIG. 4, c-di-GMP could be synthesized at a concentration as high as 10 mM using crude enzyme yPPA-tiGs3466G. The results also proved that c-di-GMP could be synthesized using the crude enzyme solution of tiGs3466G.

Example 6

Physical and Chemical Characteristics of DGC (1) Molecular Weight

As to tiGs3466G, after the purified enzyme was prepared, the molecular weight was determined by SDS-polyacrylamide gel electrophoresis. The results showed that the molecular weight was about 19800. The molecular weights of tiGs3466, yPPA-tiGs3466, and yPPA-tiGs3466G were also measured in the same manner to be about 19800 for tiGs3466 and about 52800 for yPPA-tiGs3466 and yPPA-tiGs3466G.

(2) Optimum pH

Figure 5:
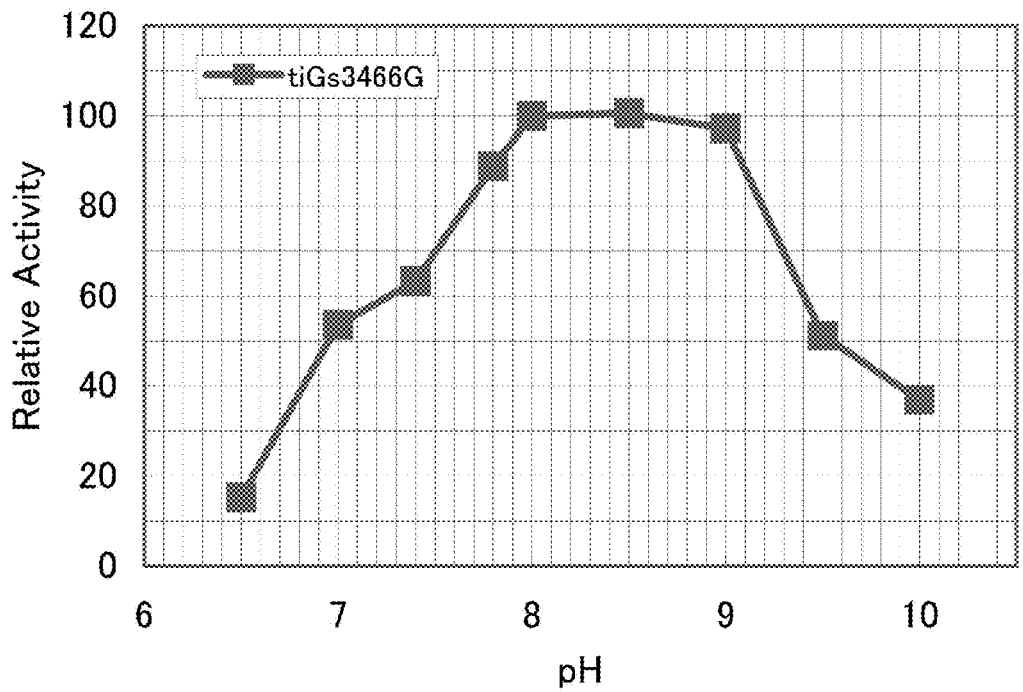
FIG. 5 is a graph showing the DGC activity of tiGs3466G at a pH ranging from 6.5 to 10.0.

As to tiGs3466G, after the purified enzyme was prepared, DGC activity was measured in the same measurement system as in Example 1 with the pH of the reaction mixture adjusted to 6.5 to 10.0. As buffers, an MES buffer, a Tris buffer, and a Glycine buffer were used. The results showed that the activity of tiGs3466G was highest at pH8.0 to 8.5. With the activity at pH8.0 being 100, the relative activity was determined, and the results are shown in Table 9 and FIG. 5. The activity of tiGs3466G at a pH ranging from 7.3 to 9.4 was not lower than 60% of the activity at pH8.0. From this, the optimum pH for tiGs3466G was evaluated to be a pH ranging from 7.3 to 9.4.

TABLE 9

|  | pH | Relative activity |
|---|---|---|
| tiGs3466G | 6.5 | 15 |
|  | 7 | 54 |
|  | 7.4 | 63 |
|  | 7.8 | 89 |
|  | 8 | 100 |
|  | 8.5 | 101 |
|  | 9 | 97 |
|  | 9.5 | 51 |
|  | 10 | 37 |

Figure 6:
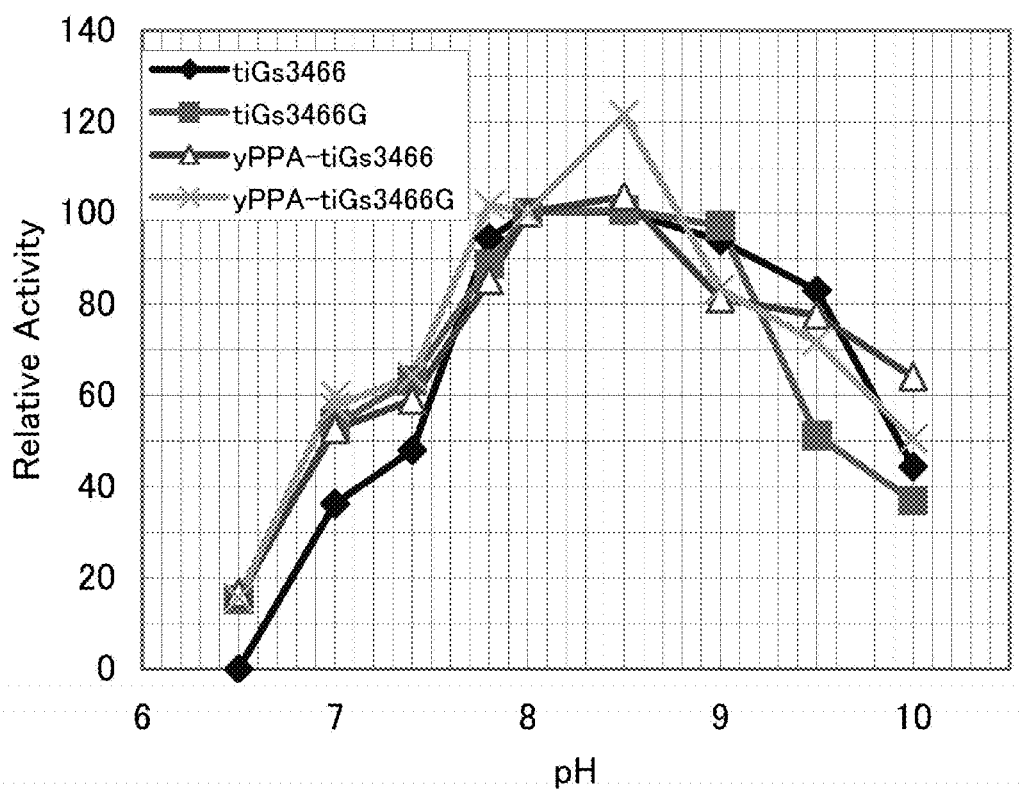
FIG. 6 is a graph showing the DGC activity of various modified enzymes in examples at a pH ranging from 6.5 to 10.0.

As to tiGs3466, yPPA-tiGs3466, and yPPA-tiGs3466G, activity at a pH ranging from 6.5 to 10.0 was measured in the same procedure as above. The results are shown in Table 10 and FIG. 6.

TABLE 10

| | pH | Relative activity |
|---|---|---|
| tiGs3466 | 6.5 | 0 |
| | 7 | 36 |
| | 7.4 | 48 |
| | 7.8 | 94 |
| | 8 | 100 |
| | 8.5 | 100 |
| | 9 | 94 |
| | 9.5 | 83 |
| | 10 | 44 |
| yPPA-tiGs3466 | 6.5 | 17 |
| | 7 | 53 |
| | 7.4 | 59 |
| | 7.8 | 85 |
| | 8 | 100 |
| | 8.5 | 104 |
| | 9 | 81 |
| | 9.5 | 78 |
| | 10 | 64 |
| yPPA-tiGs3466G | 6.5 | 16 |
| | 7 | 60 |
| | 7 | 58 |
| | 7.4 | 64 |
| | 7.8 | 102 |
| | 8 | 100 |
| | 8.5 | 122 |
| | 9 | 83 |
| | 9.5 | 72 |
| | 10 | 50 |

(3) Optimum Temperature

Figure 7:
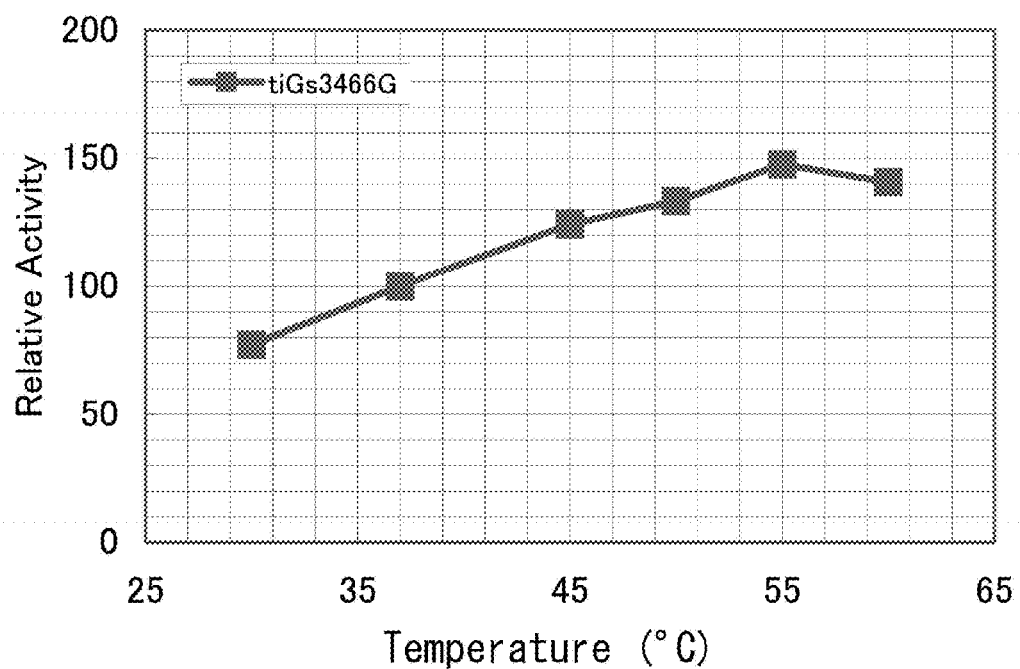
FIG. 7 is a graph showing the DGC activity of tiGs3466G at 30 to 60° C.

As to tiGs3466G, after the purified enzyme was prepared, DGC activity was measured in the same measurement system as in Example 1 with the temperature of the reaction mixture adjusted to 30 to 60° C. The results showed that the activity of tiGs3466G was highest at about 55° C. With the activity at 37° C. being 100, the relative activity was determined, and the results are shown in Table 11 and FIG. 7. The activity of tiGs3466G at 35 to 60° C. was not lower than 60% of the activity at 55° C. From this, the optimum temperature for tiGs3466G was evaluated to be 35 to 60° C.

TABLE 11

| | Temperature (° C.) | Relative Activity |
|---|---|---|
| tiGs3466G | 30 | 77 |
| | 37 | 100 |
| | 45 | 124 |

TABLE 11-continued

| | Temperature (° C.) | Relative Activity |
|---|---|---|
| | 50 | 133 |
| | 55 | 148 |
| | 60 | 141 |

Figure 8:
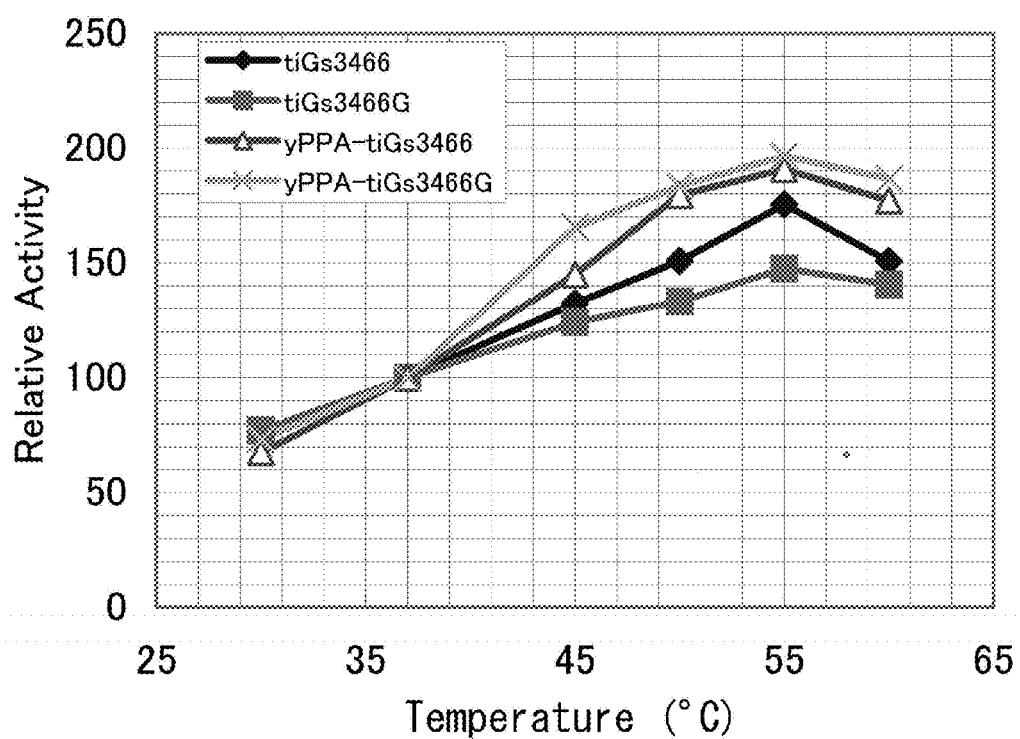
FIG. 8 is a graph showing the DGC activity of various modified enzymes in examples at 30 to 60° C.

As to tiGs3466, yPPA-tiGs3466, and yPPA-tiGs3466G, the activity at a temperature of the reaction mixture of 30 to 60° C. was measured in the same procedure as above. The results are shown in Table 12 and FIG. 8.

TABLE 12

| | Temperature (° C.) | Relative Activity |
|---|---|---|
| tiGs3466 | 37 | 100 |
| | 45 | 132 |
| | 50 | 151 |
| | 55 | 175 |
| | 60 | 151 |
| yPPA-tiGs3466 | 30 | 67 |
| | 37 | 100 |
| | 45 | 145 |
| | 50 | 179 |
| | 55 | 191 |
| | 60 | 177 |
| yPPA-tiGs3466G | 30 | 73 |
| | 37 | 100 |
| | 45 | 165 |
| | 50 | 183 |
| | 55 | 196 |
| | 60 | 187 |

Thus, the enzyme in the example with mutation of 54th residue asparagine in the amino acid sequence to glycine was remarkably enhanced in specific activity and enzymatic productivity and, in addition to this, when fused with yPPA, gave a fusion enzyme that was even more enhanced in activity. Therefore, the enzymes in the examples can significantly reduce the amount of enzyme solution required to be cultured in the step of c-di-GMP production and even eliminate the necessity for a column that is essential for purification, so that it is proved that c-di-GMP synthesis is made more practical than in conventional methods.

The present invention has been described by examples. These examples are merely exemplification, and those skilled in the art understand that various modifications can be made and these modifications are also within the scope of the present invention.

The invention claimed is:

1. A method for producing c-di-GMP from two GTP molecules using an enzyme, wherein the enzyme is a diguanylate cyclase having a molecular weight of 19,800±2,000 Da and comprising an amino acid sequence selected from the group consisting of:
   (A) the amino acid sequence of SEQ ID NO:6; and
   (B) an amino acid sequence having at least 90% identity to the amino acid sequence of SEQ ID NO:6, wherein glycine at position 54 in the amino acid of SEQ ID NO:6 is conserved and the amino acid sequence comprises a GGDEF (SEQ ID NO:26) domain or GGEEF (positions 83-87 of SEQ ID NO:6) domain comprising i-site, but lacks the amino acid sequence KXXD (SEQ ID NO: 23) in the i-site;
   the method comprising contacting two GTP molecules with said enzyme.

2. The method according to claim 1, wherein said enzyme is comprised within a fusion enzyme comprising said diguanylate cyclase and a dimerizable protein fused to the N-terminus of said diguanylate cyclase.

3. The method according to claim 2, wherein the diguanylate cyclase comprises an amino acid sequence having at least 98% identity to the amino acid sequence of SEQ ID NO:6, wherein glycine at position 54 in the amino acid of SEQ ID NO:6 is conserved and the amino acid sequence comprises a GGDEF (SEQ ID NO:26) domain or GGEEF (position 83-87 of SEQ ID NO:6) domain comprising i-site, but lacks the amino acid sequence KXXD (SEQ ID NO: 23) in the i-site, and is encoded by a modified diguanylate cyclase gene of a bacterium of the genus Geobacillus.

4. The method according to claim 2, wherein the dimerizable protein is an inorganic pyrophosphatase.

5. The method according to claim 1, wherein the diguanylate cyclase comprises the amino acid sequence of SEQ ID NO:6.

6. The method according to claim 1, wherein the diguanylate cyclase comprises an amino acid sequence having at least 98% identity to the amino acid sequence of SEQ ID NO:6, wherein glycine at position 54 in the amino acid of SEQ ID NO:6 is conserved and the amino acid sequence comprises a GGDEF (SEQ ID NO:26) domain or GGEEF (positions 83-87 of SEQ ID NO:6) domain comprising i-site, but lacks the amino acid sequence KXXD (SEQ ID NO: 23) in the i-site, and is encoded by a modified diguanylate cyclase gene of a bacterium of the genus Geobacillus.

7. The method according to claim 1, wherein the diguanylate cyclase comprises an amino acid sequence having at least 90% identity to the amino acid sequence of SEQ ID NO:6, wherein glycine at position 54 of the amino acid sequence of SEQ ID NO:6 is conserved and the amino acid sequence comprises a GGDEF (SEQ ID NO:26) domain or GGEEF (positions 83-87 of SEQ ID NO:6) domain comprising i-site, but lacks the amino acid sequence KXXD (SEQ ID NO: 23) in the i-site.

8. The method according to claim 7, wherein said diguanylate cyclase comprises an amino acid sequence having at least 95% identity to the amino acid sequence of SEQ ID NO:6, wherein glycine at position 54 of the amino acid sequence of SEQ ID NO:6 is conserved and the amino acid sequence comprises a GGDEF (SEQ ID NO:26) domain or GGEEF (position 83-87 of SEQ ID NO:6) domain comprising i-site, but the amino acid sequence lacks the amino acid sequence KXXD (SEQ ID NO: 23) in the i-site.

9. The method according to claim 1, wherein the amino acid sequence GGEEF (positions 83-87 of SEQ ID NO: 6) at positions 83-87 of the amino acid sequence of SEQ ID NO:6 is conserved.

10. The method according to claim 1, wherein the diguanylate cyclase has the following physical and chemical characteristics:
   (A) catalytic action on the reaction "2 GTP→c-di-GMP";
   (B) an optimum pH of 7.3 to 9.4 for catalytic activity;
   (C) an optimum temperature of 35 to 60° C. for catalytic activity; and
   (D) thermal stability as shown by activity of 90% or higher remaining after heating for 60 minutes at 50° C., pH7.8.

* * * * *